(12) United States Patent
Di Natali et al.

(10) Patent No.: US 10,485,409 B2
(45) Date of Patent: Nov. 26, 2019

(54) REAL-TIME POSE AND MAGNETIC FORCE DETECTION FOR WIRELESS MAGNETIC CAPSULE

(71) Applicant: Vanderbilt University, Nashville, TN (US)

(72) Inventors: Christian Di Natali, Nashville, TN (US); Marco Beccani, Viareggio (IT); Pietro Valdastri, Nashville, TN (US); Keith L. Obstein, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 401 days.

(21) Appl. No.: 14/761,577

(22) PCT Filed: Jan. 17, 2014

(86) PCT No.: PCT/US2014/012086
§ 371 (c)(1),
(2) Date: Jul. 16, 2015

(87) PCT Pub. No.: WO2014/113697
PCT Pub. Date: Jul. 24, 2014

(65) Prior Publication Data
US 2015/0342501 A1 Dec. 3, 2015

Related U.S. Application Data

(60) Provisional application No. 61/753,755, filed on Jan. 17, 2013.

(51) Int. Cl.
*A61B 5/06* (2006.01)
*A61B 5/07* (2006.01)
*A61B 1/00* (2006.01)

(52) U.S. Cl.
CPC .......... *A61B 1/00158* (2013.01); *A61B 5/062* (2013.01); *A61B 5/07* (2013.01)

(58) Field of Classification Search
CPC ..... A61B 1/00158; A61B 1/041; A61B 5/062; A61B 5/07
See application file for complete search history.

(56) References Cited

U.S. PATENT DOCUMENTS

| 3,315,660 A | 4/1967 | Abella |
| 3,858,572 A | 1/1975 | Binard et al. |

(Continued)

FOREIGN PATENT DOCUMENTS

| CN | 101778592 A | 7/2010 |
| DE | 102006019419 | 11/2007 |

(Continued)

OTHER PUBLICATIONS

Kucuk et al., "Chapter 4. Robot Kinematics: Forward and Inverse Kinematics" Industrial Robotics: Theory, Modeling and Control, textbook edited by Sam Cubero, published (2006) by Pro Literatur Verlag, Germany.*

(Continued)

*Primary Examiner* — Katherine L Fernandez
*Assistant Examiner* — Colin T. Sakamoto
(74) *Attorney, Agent, or Firm* — Michael Best & Friedrich LLP

(57) ABSTRACT

Systems and methods are described for determining an orientation and position of a capsule inserted into the body of a patient. A magnetic field is applied to an area of the patient where the capsule is located. Sensor data, including inertial data from an inertial sensor and magnetic field data indicative of the applied magnetic field as detected by at least one magnetic field sensor, is wirelessly received from the capsule. An orientation angle of the capsule is deter- (Continued)

mined based at least in part on the inertial data. The magnetic field data is compared to known characteristics of the applied magnetic field and a location of the capsule is determined based on the comparison.

14 Claims, 10 Drawing Sheets

(56) References Cited

U.S. PATENT DOCUMENTS

| | | | |
|---|---|---|---|
| 3,870,072 | A | 3/1975 | Lindemann |
| 4,048,992 | A | 9/1977 | Lindemann et al. |
| 4,207,887 | A | 6/1980 | Hiltebrandt et al. |
| 4,287,809 | A * | 9/1981 | Egli .................. F41G 3/225 324/260 |
| 4,314,251 | A * | 2/1982 | Raab .................. G01S 3/14 324/207.24 |
| 5,330,486 | A | 7/1994 | Wilk |
| 5,489,256 | A | 2/1996 | Adair |
| 6,248,080 | B1 | 6/2001 | Miesel et al. |
| 6,270,787 | B1 | 8/2001 | Ayer |
| 6,802,811 | B1 | 10/2004 | Slepian |
| 7,722,559 | B2 | 5/2010 | Uesugi et al. |
| 2001/0051766 | A1 | 12/2001 | Gazdzinski |
| 2002/0065455 | A1* | 5/2002 | Ben-Haim ......... A61N 1/36564 600/407 |
| 2003/0114731 | A1 | 6/2003 | Cadeddu et al. |
| 2003/0214580 | A1 | 11/2003 | Iddan |
| 2005/0267334 | A1 | 12/2005 | Swain et al. |
| 2005/0277852 | A1 | 12/2005 | Shih et al. |
| 2007/0221233 | A1* | 9/2007 | Kawano ............. A61B 1/00016 128/899 |
| 2008/0015413 | A1 | 1/2008 | Barlow et al. |
| 2008/0021334 | A1 | 1/2008 | Finburgh et al. |
| 2008/0058835 | A1 | 3/2008 | Farritor et al. |
| 2008/0154093 | A1 | 6/2008 | Cho et al. |
| 2008/0207999 | A1 | 8/2008 | Abraham-Fuchs et al. |
| 2008/0300458 | A1* | 12/2008 | Kim .................. A61B 1/00158 600/118 |
| 2009/0024142 | A1 | 1/2009 | Ruiz Morales |
| 2009/0054877 | A1 | 2/2009 | Hood et al. |
| 2009/0171268 | A1 | 7/2009 | Williams, Jr. et al. |
| 2009/0171373 | A1 | 7/2009 | Farritor et al. |
| 2009/0292205 | A1 | 11/2009 | Osaka |
| 2010/0100117 | A1 | 4/2010 | Brister et al. |
| 2010/0198008 | A1 | 8/2010 | Kawano |
| 2010/0256636 | A1 | 10/2010 | Fernandez et al. |
| 2011/0184235 | A1 | 7/2011 | Schostek et al. |
| 2011/0202070 | A1 | 8/2011 | Dario et al. |
| 2011/0301497 | A1* | 12/2011 | Shachar ............. A61B 1/00158 600/567 |
| 2011/0313415 | A1 | 12/2011 | Fernandez et al. |
| 2012/0035416 | A1 | 2/2012 | Fernandez et al. |
| 2012/0041345 | A1 | 2/2012 | Rajamani et al. |
| 2012/0149981 | A1 | 6/2012 | Khait et al. |
| 2012/0238796 | A1 | 9/2012 | Conlon |
| 2012/0271555 | A1 | 10/2012 | Levental et al. |
| 2013/0131695 | A1 | 5/2013 | Scarfogliero et al. |
| 2013/0165859 | A1 | 6/2013 | Imran |
| 2013/0225922 | A1 | 8/2013 | Schentag et al. |
| 2013/0245356 | A1 | 9/2013 | Fernandez et al. |
| 2013/0298715 | A1 | 11/2013 | Valdastri et al. |
| 2013/0324914 | A1 | 12/2013 | Valdastri et al. |
| 2014/0081120 | A1 | 3/2014 | Valdastri et al. |
| 2014/0081169 | A1 | 3/2014 | Gerding et al. |
| 2014/0206953 | A1 | 7/2014 | Valdastri et al. |
| 2014/0358162 | A1 | 12/2014 | Valdastri et al. |
| 2015/0045725 | A1 | 2/2015 | Smith et al. |
| 2017/0245741 | A1 | 8/2017 | Valdastri et al. |

FOREIGN PATENT DOCUMENTS

| | | |
|---|---|---|
| EP | 2163206 | 3/2010 |
| EP | 2286756 | 2/2011 |
| JP | H04144533 A | 5/1992 |
| WO | 9405200 A1 | 3/1994 |
| WO | 2000030548 | 6/2000 |
| WO | 2004041068 | 5/2004 |
| WO | 2007013059 | 2/2007 |
| WO | 2007013059 A2 | 2/2007 |
| WO | 2007146987 | 12/2007 |
| WO | 2007146987 A2 | 12/2007 |
| WO | 2008016196 A1 | 2/2008 |
| WO | 2008122997 | 10/2008 |
| WO | 2009014917 | 1/2009 |
| WO | 2010042611 | 4/2010 |
| WO | 2010042611 A1 | 4/2010 |
| WO | 2010044053 | 4/2010 |
| WO | 2010046823 | 4/2010 |
| WO | 2011058505 | 5/2011 |
| WO | 2011135503 | 11/2011 |
| WO | 2012028557 | 3/2012 |
| WO | 2012035157 | 3/2012 |
| WO | 2012080947 | 6/2012 |
| WO | 2012164517 | 12/2012 |
| WO | 2013027182 | 2/2013 |

OTHER PUBLICATIONS

PCT International Search Report and Written Opinion for Application No. PCT/US2015/049142 dated Dec. 11, 2015.

F. Carpi, N. Kastelein, M.Talcott, and C.Pappone. Magnetically controllable gastrointestinal steering ofvideo capsules. IEEE Transactions on Biomedical Engineering, 58:231-234, 2011.

J. Keller, C. Fibbe, F. Volke, J. Gerber, A. C. Masse, M. Reimann-Zawadzki, E. Rabinovitz, P. Layer,D. S. and V. Andresen, U. Rosien, and P. Swain. Inspection of the human stomach using remote controlled capsule endoscopy: a feasibility study in healthy volunteers. Gastrointestinal Endoscopy,73:22-28, 2011.

S. Park, R. Bergs, R. Eberhart, L. Baker, R. Fernandez, and J. Cadeddu. Trocar-less instrumentation forlaparoscopy: magnetic positioning of intra-abdominal camera and retractor. Annals of Surgery,245:379-384, 2007.

J. F. Rey, H. Ogata, N. Hosoe, K. Ohtsuka, N. Ogata, K. Ikeda, H. Aihara, I. Pangtay, T. Hibi, S. Kudo,and H. Tajiri. Feasibility of stomach exploration with a guided capsule endoscope. Endoscopy, 42:541-545, 2010.

P. Swain, R. Austin, K. Bally, and R. Trusty. Development and testing of a tethered, independent camera for NOTES and single-site laparoscopic procedures. Surgical Endoscopy, 24:2013-2021, 2010.

P. Valdastri, G. Ciuti, A. Verbeni, A. Menciassi, P. Dario, A. Arezzo, M. Morino. Magnetic air capsulerobotic system: Proof of concept of a novel approach for painless colonoscopy. Surgical Endoscopy,2011, in press.

G. Ostrovsky, Preview of Magnetically Guided Colonoscopy from Vanderbilt. MedGadget press release:http://medgadget.com/2011/10/preview-of-magnetically-guided-colonoscopy-from-vanderbilt.html.

A. Fritscher-Ravens, S. Fox, C.P. Swain, P. Mills, and G. Long. Cathcam guide wire-directedcolonoscopy: first pilot study in patients with a previous incomplete colonoscopy. Endoscopy, 38:209-213, 2006.

B. Vucelic, D. Rex, R. Pulanic, J. Refer, I. Hrstic, B. Levin, Z. Halpern, and N. Arber. The Aer-o-Scope: proof of concept of a pneumatic, skill-independent, self-propelling, self-navigating colonoscope.Gastroenterology, 130:672-677, 2006.

F. Cosentino, E. Tumino, G.R. Passoni, E. Morandi, and A. Capria. Functional evaluation of theEndotics System, a new disposable self-propelled robotic colonoscope: in vitro tests and clinical trial. International Journal of Artificial Organs, 32:517-527, 2009.

M. Shike, Z. Fireman, R. Eliakim, O. Segol, A. Slayer, L.B. Cohen, S. Goldfarb-Albak, and A. Repici.Sightline Colonosight system for a disposable, power-assisted, non-fiber-optic colonoscopy. Gastrointestinal Endoscopy, 68:701-710, 2008.

T. Rösch, A. Adler, H. Pohl, E. Wettschureck, M. Koch, B. Wiedenmann, and N. Hoepner. A motor-driven single-use colonoscope controlled with a hand-held device: a feasibility study involunteers. Gastrointestinal Endoscopy, 67:1139-1146, 2008.

(56) References Cited

OTHER PUBLICATIONS

A. Eickhoff, J. Van Dam, R. Jakobs, V. Kudis, D. Hartmann, U. Damian, U. Weickert, D. Schilling, andJ.F. Riemann. Computer-assisted colonoscopy (the NeoGuide endoscopy system): results of the firsthuman clinical trial (pace study). The American Journal of Gastroenterology, 102:261-266, 2007.
M. Moshkowitz, Y. Hirsch, I. Carmel, T. Duvdevany, I. Fabian, E.P. Willenz, and J. Cohen. A noveldevice for rapid cleaning of poorly prepared colons. Endoscopy, 42:834-836, 2010.
A Fritscher-Ravens, C. Mosse, T. Mills, K. Ikeda, P. Swain, Colon cleaning during colonoscopy: a newmechanical cleaning device tested in a porcine model. Gastrointestinal Endoscopy, 63:141-143, 2006.
H. Richert, B. Hilgenfeld, and P. Gomert, "Magnetic sensor techniques for new intelligent endoscopic capsules," http://www.vector-project.com/press/artikel/VECTOR%20article_Richert_MagneticSensorTechniques.pdf, publicly available prior to Sep. 17, 2012.
Than, T D.; Alici, G.; Zhou, H.; Li, W.; , "A Review of Localization Systems for Robotic Endoscopic Capsules," Biomedical Engineering, IEEE Transactions on , vol. 59, No. 9, pp. 2387-2399, Sep. 2012.
NDI Medical's Aurora product, http://www.ndigital.com/medical/products/aurora/, publicly available prior to Sep. 17, 2012.
M. B. H. Gerald Rogers. The safety of carbon dioxide insufflation during colonoscopic electro-surgical polypectomy. Gastrointestinal Endoscopy, 20:115-117, 1974.
BRACCO. Co2 efficient endoscopic insufflator.
P. E.J.-M.D. Filip Janssens, Jacques Deviere. Carbon dioxide for gut distension duringdigestive endoscopy: Technique and practice survey. World Journal of Gastroenterology, 15(12):1475-1479, 2009.
F. A. Macrae, K. G. Tan, and C. B. Williams. Towards safer colonoscopy: a report on thecomplications of 5000 diagnostic or therapeutic colonoscopies. Gut, 24(5):376{383, 1983.
W. J. R. P. Phaosawasdi K, Cooley W. Carbon dioxide-insufflated colonoscopy: an ignoredsuperior technique. Gastrointestinal Endoscopy, 32:330-333, 1986.
K. Sumanac, I. Zealley, B. M. Fox, J. Rawlinson, B. Salena, J. K. Marshall, G. W. Stevenson,and R. H. Hunt. Minimizing postcolonoscopy abdominal pain by using fCO2g insufflation: Aprospective, randomized, double blind, controlled trial evaluating a new commercially availablefCO2g delivery system. Gastrointestinal Endoscopy, 56(2):190-194, 2002.
J. C. H. Wong, K. K. Yau, H. Y. S. Cheung, D. C. T. Wong, C. C. Chung, and M. K. W. Li.Towards painless colonoscopy: A randomized controlled trial on carbon dioxide-insufflatingcolonoscopy. ANZ Journal of Surgery, 78 (10):871-874, 2008.
PCT International Search Report and Written Opinion for Application No. PCT/EP2011/064764 dated Oct. 10, 2011.
PCT International Search Report and Written Opinion for Application No. PCT/US2014/012086 dated May 14, 2014.
PCT International Search Report and Written Opinion for Application No. PCT/IB2012/052739 dated Aug. 7, 2012.
Toennies, J.L. et al., "A Wireless Insufflation System for Capsular Endoscopes," Journal of Medical Devices, vol. 3 (Jun. 2009).
Toennies, Jenna L. et al., "Initial Feasibility Studies on Wireless Insufflation of the GI Tract," IEEE International Conference on Robotics and Automation 2010—Workshop on Meso-ScaleRobotics for Medical Interventions, (May 3, 2010).
Smith, Byron, "Wireless Insufflation for Wireless Capsule Endoscopy," Vanderbilt University Master's Thesis (Aug. 2012).
Pedersen, Amanda, "Capsule Endoscopy in ER Could Drop Admission Rate," Medical Device Daily (Feb. 13, 2013).
PillCam Capsule Endoscopy products by Given Imaging, http://www.givenimaging.com/en-int/Innovative-Solutions/Capsule-Endoscopy/Pages/default.aspx, available prior to Sep. 17, 2012.
Lehman, A.C. et al., "Surgery with Cooperative Robots," Comput. Aided. Surg., 13(2), pp. 95-105 (Mar. 2008).
Cadeddu, J.A. et al., "Novel magnetically guided intra-abdominal camera to facilitate laparoendoscopic single site surgery: initial human experience," Surg. Endoscopy, 23, pp. 1984-1899 (May 9, 2009).
C. S. Bell, K. L. Obstein, P. Valdastri, "Image partitioning and illumination in image-based pose detection for teleoperated flexible endoscopes", Artificial Intelligence in Medicine, 2013, in press.
M. Beccani, C. Di Natali, L. Sliker, J. Schoen, M. E. Rentschler, P. Valdastri, "Wireless Tissue Palpation for Intraoperative Detection of Lumps in Soft Tissue", IEEE Transactions on Biomedical Engineering, 2013, in press.
M. Simi, G. Gerboni, A. Menciassi, P. Valdastri, "Magnetic Torsion Spring Mechanism for a Wireless Biopsy Capsule", ASME Journal of Medical Devices, 2013, in press.
A. Arezzo, A. Menciassi, P. Valdastri, G. Ciuti, G. Lucarini, M. Salerno, C. Di Natali, M. Verra, P. Dario, M. Morino, "Experimental assessment of a novel robotically-driven endoscopic capsule compared to traditional colonoscopy", Digestive and Liver Disease, 2013, vol. 45, N. 8, pp. 657-662.
C. Di Natali, M. Beccani, P. Valdastri, "Real-Time Pose Detection for Magnetic Medical Devices", IEEE Transactions on Magnetics, 2013, vol. 49, N. 7, pp. 3524-3527.
M. Simi, R. Pickens, A. Menciassi, S. D. Herrell, P. Valdastri, "Fine tilt tuning of a laparoscopic camera by local magnetic actuation: Two-Port Nephrectomy Experience on Human Cadavers", Surgical Innovation, 2013, vol. 20, N. 4, pp. 385-394.
J. L. Gorlewicz, S. Battaglia, B. F. Smith, G. Ciuti, J. Gerding, A. Menciassi, K. L. Obstein, P. Valdastri, R. J. Webster III, "Wireless Insufflation of the Gastrointestinal Tract", IEEE Transactions on Biomedical Engineering, 2013, vol. 60, N. 5, pp. 1225-1233.
T. Horeman, D. D. Kurteva, P. Valdastri, F. W. Jansen, J. J. van den Dobbelsteen, J. Dankelman, "The Influence of Instrument Configuration on Tissue Handling Force in Laparoscopy", Surgical Innovation, 2013, vol. 20, N. 3, pp. 260-267.
M. Simi, M. Silvestri, C. Cavallotti, M. Vatteroni, P. Valdastri, A. Menciassi, P. Dario, "Magnetically Activated Stereoscopic Vision System for Laparoendoscopic Single Site Surgery", IEEE/ASME Transactions on Mechatronics, 2013, vol. 18, N. 3, pp. 1140-1151.
K. L. Obstein, S. Battaglia, B. F. Smith, J. S. Gerding, P. Valdastri, "Novel approach for colonic insufflation via an untethered capsule (with video)", Gastrointestinal Endoscopy, 2013, vol. 77, N. 3, pp. 516-517.
K. Obstein, P. Valdastri, "Advanced Endoscopic Technologies for Colorectal Cancer Screening", World Journal of Gastroenterology, 2013, vol. 19, N. 4, pp. 431-439.
P. Valdastri, M. Simi, R. J. Webster III, "Advanced Technologies for Gastrointestinal Endoscopy", Annual Review of Biomedical Engineering, 2012, vol. 14, pp. 397-429.
G. Ciuti, N. Pateromichelakis, M. Sfakiotakis, P. Valdastri, A. Menciassi, D. P. Tsakiris, P. Dario, "A wireless module for vibratory motor control and inertial sensing in capsule endoscopy", Sensors and Actuators A: Physical, 2012, vol. 186, pp. 270-276.
P. Valdastri, G. Ciuti, A. Verbeni, A. Menciassi, P. Dario, A. Arezzo, M. Morino, "Magnetic air capsule robotic system: Proof of concept of a novel approach for painless colonoscopy", Surgical Endoscopy, 2012, vol. 26, N. 5, pp. 1238-1246.
G. Ciuti, M. Salerno, G. Lucarini, P. Valdastri, A. Arezzo, A. Menciassi, M. Morino, P. Dario, "A Comparative Evaluation of Control Interfaces for a Robotic-Aided Endoscopic Capsule Platform", IEEE Transactions on Robotics, 2012, vol. 28, N. 2, pp. 534-538.
M. Simi, N. Tolou, P. Valdastri, J. L. Herder, A. Menciassi, P. Dario, "Modeling of a Compliant Joint in a Magnetic Levitation System for an Endoscopic Camera", Mechanical Sciences, 2012, vol. 3, pp. 5-14.
M. Salerno, G. Ciuti, G. Lucarini, R. Rizzo, P. Valdastri, A. Menciassi, A. Landi, P. Dario, "A discrete-time localization method for capsule endoscopy based on on-board magnetic sensing", Measurement Science and Technology, 2012, 23 015701 (10pp).
C. Cavallotti, P. Merlino, M. Vatteroni, P. Valdastri, A. Abramo, A. Menciassi, P. Dario, "An FPGA-based flexible demo-board for endoscopic capsule design optimization", Sensors and Actuators A: Physical, 2011, vol. 172, No. 1, pp. 301-307.

(56) References Cited

OTHER PUBLICATIONS

M. Silvestri, M. Simi, C. Cavallotti, M. Vatteroni, V. Ferrari, C. Freschi, P. Valdastri, A. Menciassi, P. Dario, "Autostereoscopic Three-Dimensional Viewer Evaluation Through Comparison With Conventional Interfaces in Laparoscopic Surgery", Surgical Innovation, 2011, vol. 18, No. 3, pp. 223-230.
P. Valdastri, E. Sinibaldi, S. Caccavaro, G. Tortora, A. Menciassi, P. Dario, "A novel magnetic actuation system for miniature swimming robots", IEEE Transactions on Robotics, 2011, vol. 27, No. 4, pp. 769-779.
V. Pensabene, P. Valdastri, S. Tognarelli, A. Menciassi, A. Arezzo, P. Dario, "Mucoadhesive film for anchoring assistive surgical instruments in endoscopic surgery: in vivo assessment of deployment and attachment", Surgical Endoscopy, 2011, vol. 25, No. 9, pp. 3071-3079.
P. Valdastri, E. Susilo, T. Förster, C. Strohhöfer, A. Menciassi, P. Dario, "Wireless implantable electronic platform for chronic fluorescent-based biosensors", IEEE Transactions on Biomedical Engineering, 2011, vol. 58, No. 6, pp. 1846-1854.
M. Vatteroni, P. Valdastri, A. Sartori, A. Menciassi, P. Dario, "Linear-logarithmic CMOS pixel with tunable dynamic range", IEEE Transactions on Electron Devices, 2011, vol. 58, No. 4, pp. 1108-1115.
S. Tognarelli, V. Pensabene, S. Condino, P. Valdastri, A. Menciassi, A. Arezzo, P. Dario, "A pilot study on a new anchoring mechanism for surgical applications based on mucoadhesives", Minimally Invasive Therapy & Allied Technologies, 2011, vol. 20, No. 1, pp. 3-13.
M. Piccigallo, U. Scarfogliero, C. Quaglia, G. Petroni, P. Valdastri, A. Menciassi, P. Dario, "Design of a novel bimanual robotic system for single-port laparoscopy", IEEE/ASME Transactions on Mechatronics, 2010, vol. 15, No. 6, pp. 871-878.
M. Vatteroni, D. Covi, C. Cavallotti, P. Valdastri, A. Menciassi, P. Dario, A. Sartori, "Smart optical CMOS sensor for endoluminal applications", Sensors and Actuators A: Physical, 2010, vol. 162, No. 2, pp. 297-303.
D. Covi, C. Cavallotti, M. Vatteroni, L. Clementel, P. Valdastri, A. Menciassi, P. Dario, A. Sartori, "Miniaturized digital camera system for disposable endoscopic applications", Sensors and Actuators A: Physical, 2010, vol. 162, No. 2, pp. 291-296.
E. Buselli, V. Pensabene, P. Castrataro, P. Valdastri, A. Menciassi, P. Dario, "Evaluation of friction enhancement through soft polymer micro-patterns in active capsule endoscopy", Measurement Science and Technologies, 2010, 21 105802 (7pp).
P. Valdastri, C. Quaglia, E. Buselli, A. Arezzo, N. Di Lorenzo, M. Morino, A. Menciassi, P. Dario, "A Magnetic Internal Mechanism for Camera Steering in Wireless Endoluminal Applications", Endoscopy, 2010, vol. 42, pp. 481-486.
J. L. Toennies, G. Tortora, M. Simi, P. Valdastri, R. J. Webster III, "Swallowable Medical Devices for Diagnosis and Surgery: The State of the Art", Proceedings of the Institution of Mechanical Engineers, Part C: Journal of Mechanical Engineering Science, 2010, vol. 224, No. 7, pp. 1397-1414.
M. Simi, G. Ciuti, S. Tognarelli, P. Valdastri, A. Menciassi, P. Dario, "Magnetic link design for a robotic laparoscopic camera", Journal of Applied Physics, 2010, vol. 107, No. 9, pp. 09B302-09B302-3.
M. Simi, P. Valdastri, C. Quaglia, A. Menciassi, P. Dario, "Design, Fabrication and Testing of an Endocapsule with Active Hybrid Locomotion for the Exploration of the Gastrointestinal Tract", IEEE Transactions on Mechatronics, 2010, vol. 15, No. 2, pp. 170-180.
G. Ciuti, R. Donlin, P. Valdastri, A. Arezzo, A. Menciassi, M. Morino, P. Dario, "Robotic versus manual control in magnetic steering of an endoscopic capsule", Endoscopy, 2010, vol. 42, pp. 148-152.
G. Ciuti, P. Valdastri, A. Menciassi, P. Dario, "Robotic magnetic steering and locomotion of capsule endoscope for diagnostic and surgical endoluminal procedures", Robotica, 2010, vol. 28, No. 2, pp. 199-207.
R. Carta, G. Tortora, J. Thone, B. Lenaerts, P. Valdastri, A. Menciassi, R. Puers, P. Dario, "Wireless powering for a self-propelled and steerable endoscopic capsule for stomach inspection", Biosensors and Bioelectronics, 2009, vol. 25, No. 4, pp. 845-851.
C. Quaglia, E. Buselli, R. J. Webster III, P. Valdastri, A. Menciassi, P. Dario, "An Endoscopic Capsule Robot: A Meso-Scale Engineering Case Study", Journal of Micromechanics and Microengineering, 2009, vol. 19, No. 10, 105007 (11pp).
G. Tortora, P. Valdastri, E. Susilo, A. Menciassi, P. Dario, F. Rieber, M. O. Schurr, "Propeller-based wireless device for active capsular endoscopy in the gastric district", Minimally Invasive Therapy & Allied Technologies, 2009, vol. 18, No. 5, pp. 280-290.
E. Susilo, P. Valdastri, A. Menciassi, P. Dario, "A Miniaturized Wireless Control Platform for Robotic Capsular Endoscopy Using Advanced Pseudokernel Approach", Sensors and Actuators A: Physical, 2009, vol. 156, No. 1, pp. 49-58.
C. Cavallotti, M. Piccigallo, E. Susilo, P. Valdastri, A. Menciassi, P. Dario, "An Integrated Vision System with Autofocus for Wireless Capsular Endoscopy", Sensors and Actuators A: Physical, 2009, vol. 156, No. 1, pp. 72-78.
P. Valdastri, R. J. Webster III, C. Quaglia, M. Quirini, A. Menciassi, P. Dario, "A New Mechanism for Meso-Scale Legged Locomotion in Compliant Tubular Environments", IEEE Transactions on Robotics, 2009, vol. 25, No. 5, pp. 1047-1057.
International Search Report, PCT/US2014/012086, dated May 14, 2014.
Written Opinion, PCT/US2014/012086, dated May 14, 2014.
P. Valdastri, S. Tognarelli, A. Menciassi, P. Dario, "A scalable platform for biomechanical studies of tissue cutting forces", Measurement Science and Technology, 2009, vol. 20, 045801 (11pp).
E. Buselli, P. Valdastri, M. Quirini, A. Menciassi, P. Dario, "Superelastic leg design optimization for an endoscopic capsule with active locomotion", Smart Materials and Structures, 2009, vol. 18, 015001 (8pp).
P. Valdastri, C. Quaglia, E. Susilo, A. Menciassi, P. Dario, C.N. Ho, G. Anhoeck, M.O. Schurr, "Wireless Therapeutic Endoscopic Capsule: in-vivo Experiment", Endoscopy, 2008, vol. 40, pp. 979-982.
P. Valdastri, A. Menciassi, P. Dario, "Transmission Power Requirements for Novel ZigBee Implants in the Gastrointestinal Tract", IEEE Transactions on Biomedical Engineering, 2008, vol. 55, No. 6, pp. 1705-1710.
P. Valdastri, S. Rossi, A. Menciassi, V. Lionetti, F. Bernini, F. A. Recchia, P. Dario, "An Implantable ZigBee Ready Telemetric Platform for In Vivo Monitoring of Physiological Parameters", Sensors and Actuators A: Physical, 2008, vol. 142, No. 1, pp. 369-378.
A. Sieber, P. Valdastri, K. Houston, C. Eder, O. Tonet, A. Menciassi, P. Dario, "A Novel Haptic Platform for Real Time Bilateral Biomanipulation with a MEMS Sensor for Triaxial Force Feedback", Sensors and Actuators A: Physical, 2008, vol. 142, No. 1, pp. 19-27.
A. Sieber, P. Valdastri, K. Houston, A. Menciassi, P. Dario, "Flip Chip Microassembly of a Silicon Triaxial Force Sensor on Flexible Substrates", Sensors and Actuators A: Physical, 2008, vol. 142, No. 1, pp. 421-428.
L. Beccai, S. Roccella, L. Ascari, P. Valdastri, A. Sieber, M. C. Carrozza, P. Dario, "Development and Experimental Analysis of a Soft Compliant Tactile Microsensor to be Integrated in an Antropomorphic Artificial Hand", IEEE/ASME Transactions on Mechatronics, 2008, vol. 13, No. 2, pp. 158-168.
C. Oddo, P. Valdastri, L. Beccai, S. Roccella, M.C. Carrozza, P. Dario, "Investigation on calibration methods for multi-axis, linear and redundant force sensors", Measurement Science and Technology, 2007, vol. 18, pp. 623-631.
P. Valdastri, K. Houston, A. Menciassi, P. Dario, A. Sieber, M. Yanagihara, M. Fujie, "Miniaturised Cutting Tool with Triaxial Force Sensing Capabilities for Minimally Invasive Surgery", ASME Journal of Medical Devices, 2007, vol. 1, N. 3, pp. 206-211.
G. Turchetti, B. Labella, P. Valdastri, A. Menciassi, P. Dario, "The importance of giving an alternative: the case of fetal surgery", Int. J. Healthcare Technology and Management, 2007, vol. 8, Nos. 3-4, pp. 250-267.
P. Valdastri, K. Harada, A. Menciassi, L. Beccai, C. Stefanini, M. Fujie, and P. Dario, "Integration of a Miniaturised Triaxial Force Sensor in a Minimally Invasive Surgical Tool", IEEE Transactions on Biomedical Engineering, 2006, vol. 53, No. 11, 2397-2400.

(56) References Cited

OTHER PUBLICATIONS

P. Valdastri, P. Corradi, A. Menciassi, T. Schmickl, K. Crailsheim, J. Seyfried, P. Dario, "Micromanipulation, Communication and Swarm Intelligence Issues in a Swarm Microrobotic Platform", Robotics and Autonomous Systems, 2006, vol. 54, No. 10, pp. 789-804.

P. Valdastri, S. Roccella, L. Beccai, E. Cattin, A. Menciassi, M. C. Carrozza, P. Dario, "Characterization of a novel hybrid silicon three-axial force sensor", Sensors and Actuators A: Physical, 2005, vol. 123-124C, pp. 249-257.

L. Beccai, S. Roccella, A. Arena, F. Valvo, P. Valdastri, A. Menciassi, M. C. Carrozza, P. Dario, "Design and fabrication of a hybrid silicon three axial force sensor for biomechanical applications", Sensors and Actuators A: Physical, 2005, vol. 120, No. 2, pp. 370-382.

P. Valdastri, A. Menciassi, A. Arena, C. Caccamo, and P. Dario, "An Implantable Telemetry Platform System for in vivo Monitoring of Physiological Parameters", IEEE Transactions on Information Technology in Biomedicine, 2004, vol. 8, No. 3, pp. 271-278.

X. Wang, C. Di Natali, M. Beccani, M. Kern, P. Valdastri, M. Rentschler, "Novel Medical Wired Palpation Device: A Device Validation Study of Material Properties", Transducers 2013, Barcelona, Spain, pp. 1653-1658.

M. Beccani, C. Di Natali, M. E. Rentschler, P. Valdastri, "Wireless Tissue Palpation: Proof of Concept for a Single Degree of Freedom", IEEE International Conference on Robotics and Automation (ICRA) 2013, Karlsruhe, Germany, pp. 703-709.

M. Beccani, C. Di Natali, M. Rentschler, P. Valdastri, "Uniaxial Wireless Tissue Palpation Device for Minimally Invasive Surgery", ASME Design of Medical Devices Conference, Apr. 2013, Minneapolis, Minnesota, ASME Journal of Medical Devices, vol. 7, N. 2, 020919 (3 pp).

C. Di Natali, P. Valdastri "Remote active magnetic actuation for a single-access surgical robotic manipulator", in Proc. of the XVI Annual Conference of the International Society for Computer Aided Surgery (ISCAS) 2012, Pisa, Italy, Jun. 2012, International Journal of Computer Assisted Radiology and Surgery, 2012, vol. 7, Suppl. 1, pp. S169-S170.

C. Di Natali, T. Ranzani, M. Simi, A. Menciassi, P. Valdastri "Trans-abdominal Active Magnetic Linkage for Robotic Surgery: Concept Definition and Model Assessment", in Proc. of IEEE International Conference on Robotics and Automation (ICRA) 2012, St Paul, MN, USA, May 2012, pp. 695-700.

M. Simi, G. Gerboni, A. Menciassi, P. Valdastri, "Magnetic Mechanism for Wireless Capsule Biopsy", in Proc. of ASME Design of Medical Devices Conference, Apr. 10-12, 2012, Minneapolis, MN, ASME Journal of Medical Devices, vol. 6, p. 017611-1.

T. Ranzani, C. Di Natali, M. Simi, A. Menciassi, P. Dario, P. Valdastri, "A Novel Surgical Robotic Platform Minimizing Access Trauma", in Proc. of 4th Hamlyn Symposium on Medical Robotics, London, UK, Jun. 2011, pp. 15-16.

P. Valdastri, G. Ciuti, A. Verbeni, A. Menciassi, P. Dario, A. Arezzo, M. Morino, "Magnetic air capsule robotic system: a novel approach for painless colonoscopy", 19th International Congress of the European Association of Endoscopic Surgery (EAES) in Turin, Italy.

M. Simi, G. Sardi, P. Valdastri, A. Menciassi, P. Dario, "Magnetic Levitation Camera Robot for Endoscopic Surgery", in Proc. of IEEE International Conference on Robotics and Automation (ICRA) 2011, Shanghai, China, May 2011, pp. 5279-5284.

O. Alonso, J. Canals, L. Freixas, J. Samitier, A. Dieguez, M. Vatteroni, E. Susilo, C. Cavallotti, P. Valdastri, "Enabling multiple robotic functions in an endoscopic capsule for the entire gastrointestinal tract exploration", in Proc. ESSCIRC, 2010, pp. 386-389.

J. L. Toennies, G. Ciuti, B. F. Smith, A. Menciassi, P. Valdastri, and Robert J. Webster III, "Toward Tetherless Insufflation of the GI Tract", in Proc. IEEE Engineering in Medicine and Biology Society Conference (EMBC) 2010, Buenos Aires, Argentina, Sep. 2010, pp. 1946-1949.

G. Tortora, S. Caccavaro, P. Valdastri, A. Menciassi, P. Dario, "Design of an autonomous jellyfish miniature robot based on a novel concept of magnetic actuation", in Proc. of IEEE International Conference on Robotics and Automation (ICRA) 2010, Anchorage, AK, USA, May 2010, pp. 1592-1597.

L. S. Chiang, P. S. Jay, P. Valdastri, A. Menciassi, P. Dario, "Tendon Sheath Analysis for Prediction of Distal End Force and Elongation", in Proc. IEEE/ASME Conference on Advanced Intelligent Mechatronics 2009, Singapore, Jul. 2009, pp. 332-337.

O. Tonet, M. Marinelli, G. Megali, A. Sieber, P. Valdastri, A. Menciassi, P. Dario, "Control of a teleoperated nanomanipulator with time delay under direct vision feedback", in Proc. of IEEE International Conference on Robotics and Automation (ICRA) 2007, Rome, Italy, Apr. 2007, pp. 3514-3519.

J. L. Toennies, R. J. Webster III, P. Valdastri, "Mesoscale Mobile Robots for Gastrointestinal Minimally Invasive Surgery (MIS)", Chapter 10, pp. 224-251, in "Medical Robotics—Minimally Invasive Surgery" edited by Paula Gomes, Woodhead Publishing Series in Biomaterials: No. 51, ISBN 0-85709-130-1 (Aug. 2012).

A. Menciassi, P. Valdastri, K. Harada, P. Dario, "Single and Multiple Robotic Capsules for Endoluminal Diagnosis and Surgery", Chapter 14, pp. 313-354, in "Surgical Robotics—System Applications and Visions", edited by J. Rosen, B. Hannaford, R. Satava, published by Springer, 1st Edition, 2011, XXII, 819 p. 365 illus, Hardcover, ISBN: 978-1-4419-1125-4.

B. Laulicht, N. Gidmark, A. Tripathl, E. Mathiowitz, "Localization of magnetic pills," Proc. of the National Academy of Sciences, vol. 108, No. 6, 2252-2257 (Feb. 8, 2011).

"S. Best, E. Olweny, S. Park, P. Smith, R. Fernandez, D. Scott, R. Bergs, and J. Cadeddu. Newgeneration magnetic camera facilitates porcine LESS nephrectomy. The Journal of Urology, 185:e413-e413, 2011."

Simaan, "Snake-Like Units Using Flexible Backbones and Actuation Redundancy for Enhanced Miniaturization," in IEEE International Conference on Robotics and Automation, 2005, pp. 3020-3028.

Song et al., "Mechanical properties of the human abdominal wall measured in vivo during insufflation for laparoscopic surgery," Surgical Endoscopy, vol. 20, No. 6, pp. 987-990, 2006.

Sonnenberg et al., "Is virtual colonoscopy a cost-effective option to screen for colorectal cancer?" Am J Gastroenterol. Aug. 1999;94(8):2268-74.

Sosna et al., "Colonic perforation at CT colonography:assessment of risk in a multicenter large cohort," Radiology. 2006; 239(2):457-63.

Stark et al., "The future of telesurgery: a universal system with haptic sensation," Journal of the Turkish-German Gynecological Association, vol. 13, No. 1, pp. 74-76, 2012.

Stevension, "Pain following colonoscopy: elimination with carbon dioxide," Gastrointestinal Endoscopy, pp. 564-567, 1992.

Takktile by Y. Tenzer, L. Jentoft, I. Daniher, and Robert Howe: www.takktile.com.

The Center for Disease Control and Prevention, "Colorectal cancer screening basic fact sheet," 2017, 2 pages.

Tholey et al., "A compact and modular laparoscopic grasper with tri-directional force measurement capability," ASME Journal of Medical Devices, vol. 2, No. 3, pp. 031 001-9, 2008.

Tully et al., "Constrained Filtering with Contact Detection Data for the Localization and Registration of Continuum Robots in Flexible Environments," Proceedings—IEEE International Conference on Robotics and Automation, 2012, 3388-3394.

Van Der Meijden et al., "The value of haptic feedback in conventional and robot-assisted minimal invasive surgery and virtual reality training: a current review," Surgical Endoscopy, vol. 23, pp. 1180-1190, 2009.

Varadarajulu et al., "GI Endoscopes," Gastrointestinal Endoscopy, vol. 74, No. 1, pp. 1-6.e6, Jul. 2011.

Webster et al., "Design and Kinematic Modeling of Constant Curvature Continuum Robots: A Review," The International Journal of Robotics Research, vol. 29, No. 13, pp. 1661-1683, Jun. 2010.

Webster et al., "Mechanics of Precurved-Tube Continuum Robots," IEEE Transactions on Robotics, vol. 25, No. 1, pp. 67-78, Feb. 2009.

(56) References Cited

OTHER PUBLICATIONS

Wellman et al., "Extracting Features from Tactile Maps," Proceedings of the Second International Conference on Medical Image Computing and Computer-Assisted Intervention, vol. 167, pp. 11-1142, 1999.
Wellman et al., "Tactile Imaging of Breast Masses: First Clinical Report," vol. 136, No. 2, pp. 204-248, 2001.
Wellman et al., "Tactile imaging: a method for documenting breast lumps," 1999, vol. 2, p. 1131.
White et al., "Surgical Technique: Static Intramedullary Nailing of the Femur and Tibia Without Intraoperative Fluoroscopy.," Clinical orthopaedics and related research, pp. 3469-3476, Mar. 2011.
Wilhelm et al., "Gastrointestinal Endoscopy in a Low Budget Context: Delegating EGD to Non-Physician Clinicians in Malawi can be Feasible and Safe." Endoscopy, vol. 44, No. 2, pp. 174-176, Feb. 2012.
Wilkins et al., The current state of flexible sigmoidoscopy training in family medicine residency programs. Family Medicine, 37:706-11, 2005.
Wilkins et al., "Colorectal cancer: A summary of the evidence for screening and prevention," Am Fam Physician. Dec. 15, 2008;78(12):1385-1392.
Xu et al., "Actuation Compensation for Flexible Surgical Snake-like Robots with Redundant Remote Actuation," in IEEE International Conference on Robotics and Automation, 2006, pp. 4148-4154.
Xu et al., "An Investigation of the Intrinsic Force Sensing Capabilities of Continuum Robots," IEEE Transactions on Robotics, vol. 24, No. 3, pp. 576-587, 2008.
Xu et al., "Analytic Formulation for Kinematics, Statics and Shape Restoration of Multibackbone Continuum Robots via Elliptic Integrals," ASME Journal of Mechanisms and Robotics (JMR), vol. 2, pp. 11006-11013, 2010.
Xu et al., "Intrinsic Wrench Estimation and Its Performance Index for Multisegment Continuum Robots," IEEE Transactions on Robotics, vol. 26, No. 3, pp. 555-561, Jun. 2010.
Xu, "Design, Modeling and Analysis of Continuum Robots as Surgical Assistants with Intrinsic Sensory Capabilities," Ph.D. Dissertation, (Advisor: N. Simaan), Mechanical Engineering, Columbia University, 2009, 1-24.
Yamamoto et al., "Techniques for Environment Parameter Estimation During Telemanipulation," pp. 217-223, 2008.
Yim et al., "Biopsy Using a Magnetic Capsule Endoscope Carrying, Releasing, and Retrieving Untethered Microgrippers." IEEE Trans. Biomed. Eng., vol. 61, No. 2, pp. 513-521, Feb. 2014.
Yim et al., "Design and Analysis of a Magnetically Actuated and Compliant Capsule Endoscopic Robot," 2011 IEEE Int. Conf. Robot. Autom., pp. 4810-4815, May 2011.
Yim et al., "Magnetically Actuated Soft Capsule With the Multimodal Drug Release Function," IEEE/ASME Trans. Mechatronics, vol. 18, No. 4, pp. 1413-1418, 2013.
Chinese Patent Office Action for Application No. 201580060855.6 dated Jul. 3, 2018, 8 pages. No translation.
European Patent Office Search Report for Application No. 15840650.4 dated May 28, 2018, 8 pages.
Keller et al., "Method for Navigation and Control of a Magnetically Guided Capsule Endoscope in the Human Stomach," Proc. of the IEEE RAS and EMBS Int. Conf. on Biomedical Robotics and Biomechatronics, pp. 859-865, 2012.
Kong et al., "A rotational micro biopsy device for the capsule endoscope," Intelligent robots and systems. In Intelligent Robots and Systems, 2005; 1839-1843.
Koulaouzidis et al., "Capsule Endoscopy in Clinical Practice: Concise Up-To-Date Overview." Clinical and Experimental Gastroenterology, vol. 2, pp. 111-116, Jan. 2009.
Kubler et al., "Development of actuated and sensor integrated forceps for minimally invasive robotic surgery," The International Journal of Medical Robotics and Computer Assisted Surgery, vol. 1, No. 3, pp. 96-107, 2005.
Kunkel et al., "Using robotic systems in order to determine biomechanical properties of soft tissues," in Studies in Health Technology and Informatics, Proceedings of the 2nd Conference on Applied Biomechanics, vol. 133, No. 3, 2008, p. 156.
Lederman et al., "Force variability during surface contact with bare finger or rigid probe," 12th International Symposium on Haptic Interfaces for Virtual Environment and Teleoperator Systems, 2004. HAPTICS '04. Proceedings., pp. 154-160, 2004.
Lee et al., "Gastric Cancer Screening and Subsequent Risk of Gastric Cancer: A Large-Scale Population-Based Cohort Study, with a 13-Year Follow-Up in Japan," Int. J. Cancer, vol. 118, No. 9, pp. 2315-2321, May 2006.
Leung et al., "Impact of a novel water method on scheduled unsedated colonoscopy in U.S. veterans," Gastrointestinal Endoscopy, 69(3, Part 1):546-550, 2009.
Li et al., "Diagnostic value of fecal tumor m2-pyruvate kinase for crc screening: a systematic review and meta-analysis," Int J Cancer. Oct. 15, 2012;131(8):1837-45.
Lister et al., "Development of in vivo constitutive models for liver: Application to surgical simulation," Annals of Biomedical Engineering, vol. 39, pp. 1060-1073, 2011.
Liu et al., "A haptic probe for soft tissue abnormality identification during minimally invasive surgery," 2009, pp. 417-422.
Liu et al., "Experimental study of soft tissue recovery using optical fiber probe," 2007, pp. 516-521.
Liu et al., "Rolling indentation probe for tissue abnormality identification during minimally invasive surgery," IEEE Trans. Robot., vol. 27, No. 3, pp. 450-460, 2011.
Liu et al., "Rolling Mechanical Imaging: A Novel Approach for Soft Tissue Modeling and Identification during Minimally Invasive Surgery," 2008, pp. 845-849.
Makuuchi et al., "Endoscopic Screening for Esophageal Cancer in 788 Patients with Head and Neck Cancers," The Tokai Journal of Experimental and Clinical Medicine, vol. 21, pp. 139-145, 1996.
Mayo Clinic Health System, "EGD—Mayo Clinic Health System," 2013. [Online]. Available: http://mayoclinichealthsystem.org/locations/eau-claire/medical-services/gastroenterology-and-hepatology/egd.
McCreery et al., "Feasibility of locating tumours in lung via kinaesthetic feedback." The International Journal of Medical Robotics and Computer Assisted Surgery, vol. 4, No. 1, pp. 58-68, 2008.
Miller et al., "Tactile imaging system for localizing lung nodules during video assisted thoracoscopic surgery," 2007, pp. 2996-3001.
Mishkin et al., "ASGE Technology Status Evaluation Report: Wireless Capsule Endoscopy" Gastrointestinal Endoscopy, vol. 63, No. 4, pp. 539-545, Apr. 2006.
Mishra et al., "Environment Parameter Estimation during Bilateral Telemanipulation," in IEEE Virtual Reality Conference (VR'06), 2006, No. 1, pp. 100-100.
Moll et al., "Reconstructing shape from motion using tactile sensors," 2001, vol. 2, pp. 692-700.
Naish et al., "Effect of Velocity Control on Kinesthetic Lung Tumour Localization," in 21st Canadian Conference on Electrical and Computer Engineering, 2008, vol. 1345, pp. 1337-1340.
National Digestive Diseases Information Clearinghouse, https://www.niddk.nih.gov/health-information/digestive-diseases.
Noonan et al., "A dual-function wheeled probe for tissue viscoelastic property identification during minimally invasive surgery," 2007, pp. 2629-2634.
Ohtsuka et al., "Application of a new tactile sensor to thoracoscopic surgery: Experimental and clinical study," The Annals of Thoracic Surgery, vol. 60, No. 3, pp. 610-614, 1995.
Okamura et al., "Feature Guided Exploration with a Robotic Finger," 2001, pp. 589-596.
Okamura et al., "Overview of dexterous manipulation," 2000, vol. 1, pp. 255-262.
Oshima et al., "Evaluation of a Mass Screening Program for Stomach Cancer with a Casecontrol Study Design," Int. J. Cancer, vol. 38, No. 6, pp. 829-833, Dec. 1986.
Ottensmeyer et al., "In vivo data acquisition instrument for solid organ mechanical property measurement," in Medical Image Computing and Computer-Assisted Intervention—MICCAI 2001. Springer, 2001, pp. 975-982.
Patterson et al., "The Pig as an Experimental Model for Elucidating the Mechanisms Governing Dietary Influence on Mineral Absorption," Experimental biology and medicine, 2008; 233(6):651-64.

(56) References Cited

OTHER PUBLICATIONS

Pilz et al., "Colon capsule endoscopy compared to conventional colonoscopy under routine screening conditions," BMC Gastroenterology, 2010; 10:66.

Puangmali et al., "Miniature 3-axis distal force sensor for minimally invasive surgical palpation," IEEE/ASME Trans. Mechatronics, vol. 17, No. 4, pp. 646-656, 2012.

Puangmali et al., "Optical Fiber Sensor for Soft Tissue Investigation during Minimally Invasive Surgery," in 2008 IEEE International Conference on Robotics and Automation, 2008, pp. 2934-2938.

Quirini et al., Feasibility proof of a legged locomotion capsule for the GI tract. Gastrointestinal Endoscopy, 67:1153-1158, 2008.

Randolph et al., "Recurrent laryngeal nerve identification and assessment during thyroid surgery: laryngeal palpation," World journal of surgery, vol. 28, No. 8, pp. 755-760, Aug. 2004.

Rosen et al., "Biomechanical properties of abdominal organs in vivo and postmortem under compression loads," Journal of Biomechanical Engineering, vol. 130, No. 021020, pp. 1-17, 2008.

Rucker et al., "A Geometrically Exact Model for Externally Loaded Concentric-Tube Continuum Robots.," IEEE transactions on robotics : a publication of the IEEE Robotics and Automation Society, vol. 26, No. 5, pp. 769-780, Jan. 2010.

Rucker et al., "Computing Jacobians and compliance matrices for externally loaded continuum robots," in 2011 IEEE International Conference on Robotics and Automation, 2011, No. 3, pp. 945-950.

Rucker et al., "Equilibrium Conformations of Concentric-tube Continuum Robots," The International Journal of Robotics Research, vol. 29, No. 10, pp. 1263-1280, Apr. 2010.

Sabatini et al., "Interpretation of mechanical properties of soft tissues from tactile measurements," vol. 139, 1990, pp. 152-162.

Samur et al., "A robotic indenter for minimally invasive measurement and characterization of soft tissue response," Medical Image Analysis, vol. 11, No. 4, pp. 361-373, 2007.

Sangpradit et al., "Tissue identification using inverse finite element analysis of rolling indentation," 2009, pp. 1250-1255.

Sauk et al., Optical enhancements in diagnosis and surveillance of colorectal neoplasia.

Sauk et al., "Optical enhancements in diagnosis and surveillance of colorectal neoplasia," Curr Colorectal Cancer Rep, 2011; 7: 24-32.

Scheidler et al., "Virtual colonoscopy using CT and MRI," Radiologe, 38(10):824-31, 1998.

Schindler et al., "Foaming at the mouth: Ingestion of Hydrogen Peroxide Solution (with video)," Clinical gastroenterology and hepatology, Feb. 2012; 10(2): e13-4.

Segnan et al., "Comparing attendance and detection rate of colonoscopy with sigmoidoscopy and FIT for colorectal cancer screening," Gastroenterology, 2007; 132(7): 2304-2312.

Seidell, Solubilities of inorganic and organic substances. New York, D. Van Nostrand company, 2nd edition, 1907.

Shaker et al., Principles of Deglutition. Springer Science & Business Media, 2012.

Simaan et al., "Design and Integration of a Telerobotic System for Minimally Invasive Surgery of the Throat," International Journal of Robotics Research—special issue on Medical Robotics (special Issue on Medical Robotics), vol. 28, No. 9, pp. 1134-1153, 2009.

Adami et al., "Primary and Secondary Prevention in the Reduction of Cancer Morbidity and Mortality." Eur. J. Cancer, vol. 37 Suppl 8, pp. S118-S127, 2001.

Zbyszewski et al., "Air-cushion force sensitive probe for soft tissue investigation during minimally invasive surgery," 2008, pp. 827-830.

American Cancer Society, "Cancer Facts & Figures 2005," 2005.

American Cancer Society, "What are the key statistics about colorectal cancer?" http://www.cancer.org/Cancer/ColonandRectumCancer/DetailedGuide/colorectal-cancer-key-statistics. Jun. 2012.

Arber et al., Proof-of-concept study of the aer-o-scope omnidirectional colonoscopic viewing system in ex vivo and in vivo porcine models. Endoscopy, 39(5):412-417, May 2007.

Ascari et al., "A New Active Microendoscope for Exploring the Subarachnoid Space in the Spinal Cord," 2003 IEEE Int. Conf. Robot. Autom., vol. 2, pp. 2657-2667, 2003.

Bajo et al., "Configuration and Joint Space Feedback for Improved Accuracy of Continuum Robots," in IEEE International Conference on Robotics and Automation, 2011, pp. 2905-2912.

Bajo et al., "Finding Lost Wrenches: Using Continuum Robots for Contact Detection and Estimation of Contact Location," in 2010 IEEE International Conference on Robotics and Automation, 2010, pp. 3666-3673.

Bajo et al., "Integration and Preliminary Evaluation of an Insertable Robotic Effectors Plafform for Single Port Access Surgery," IEEE International Conference on Robotics and Automation, Saint Paul, MN, 2012, pp. 3381-3387.

Bajo et al., "Kinematics-Based Detection and Localization of Contacts Along Multisegment Continuum Robots," IEEE Transactions on Robotics, 2012; 28(2): 291-302.

Bhattacharyya, "Motion Planning and Constraint Exploration for Robotic Surgery," M.Sc. thesis, (Advisor: N. Simaan), Mechanical Engineering, Vanderbilt University, 2011; 1-130.

Bray et al., "Global Cancer Transitions According to the Human Development Index: A Population-Based Study," The Lancet Oncology,2012; 13: 790-801.

Burgner et al., "A bimanual teleoperated system for endonasal skull base surgery," in 2011 IEEE/RSJ International Conference on Intelligent Robots and Systems, 2011, pp. 2517-2523.

Burling et al., Automated Insufflation of Carbon Dioxide for MDCT Colonography: Distension and Patient Experience Compared with Manual Insufflation. Journal of Radiology, 2006; 186: 96-103.

Castanheira et al., "Fluorescence and diffuse reflectance spectroscopy for early cancer detection using a new strategy towards the development of a miniaturized system," IEEE Engineering in Medicine and Biology Society. Conference. 2010. 1210-3.

Ciuti, "Innovative control platforms for robotic microsystems in endoluminal surgery," Masters thesis, Scuola Superiore di Studi Universitari e Perfezionamento Sant' Anna, 2012.

Clark, Anatomy and Physiology: Understanding the Human Body. Sudbury,MA: Jones and Bartlett, 2005.

Classen, Gastroenterological Endoscopy. Thieme Medical Publishers, 2010.

Conway et al., "Endoscopic hemostatic devices," Gastrointest Endosc. 2009; 69(6):987-96.

Culmer et al., "Reviewing the technological challenges associated with the development of a laparoscopic palpation device," The International Journal of Medical Robotics and Computer Assisted Surgery, vol. 8, No. 2, pp. 146-159, 2012.

Dario et al., "An advanced robot system for automated diagnostic tasks through palpation," IEEE Trans. Biomed. Eng., vol. 35, No. 2, pp. 118-126, 1988.

Davila et al., "ASGE guideline: colorectal cancer screening and surveillance," American Society for Gastrointestinal Endoscopy, 2006; 63(4): 546-557.

De Falco et al., "An Integrated System for Wireless Capsule Endoscopy in a Liquid-Distended Stomach," IEEE Trans. Biomed. Eng., vol. 61, No. 3, pp. 794-804, Mar. 2013.

Dellon et al., "The use of carbon dioxide for insufflation during GI endoscopy: a systematic review," Gastrointestinal Endoscopy, 69:843-849, 2009.

Dietzel et al., "Magnetic active agent release system (maars): Evaluation of a new way for a reproducible, externally controlled drug release into the small intestine," J Control Release. Aug. 10, 2012;161(3):722-7.

Dupont et al., "Design and Control of Concentric-Tube Robots.," IEEE transactions on robotics : a publication of the IEEE Robotics and Automation Society, vol. 26, No. 2, pp. 209-225, Apr. 2010.

Edwards et al., "Annual report to the nation on the status of cancer, 1975-2006, featuring colorectal cancer trends and impact of interventions (risk factors, screening, and treatment) to reduce future rates," Cancer, pp. 544-574, 2010.

Egorov et al., "Mechanical Imaging of the Breast," vol. 27, No. 9, pp. 1275-1287, 2008.

Egorov et al., "Prostate mechanical imaging: 3-D image composition and feature calculations," vol. 25, No. 10, pp. 1329-1340, 2006.

(56) References Cited

OTHER PUBLICATIONS

Faigel, Endoscopic Oncology: Gastrointestinal Endoscopy and Cancer Management. Humana Press, 2006.
Ferlay et al., "Globocan 2012, Cancer Incidence and Mortality Worldwide: IARC Cancer Base," 2013.
Ferro et al., "Worldwide Trends in Gastric Cancer Mortality (1980-2011), with Predictions to 2015, and Incidence by Subtype," Eur. J. Cancer, vol. 50, No. 7, pp. 1330-1344, May 2014.
Fleming et al., The safety of helim for abdominal insufflation. Surgical Endoscopy, 11:230-234 230-234, 1997.
Fuller et al., "Laparoscopic trocar injuries: A report from a U.S. Food and Drug Administration (FDA) Center for Devices and Radiological Health (CDRH) Systematic Technology Assessment of Medical Products (STAMP) committee," 2003, www.fda.gov/medicaldevices/safety/alertsandnotices/ucm197339.htm.
Furlani, Permanent Magnet and Electromechanical Devices. Academic Press, 2001, pp. 131-135.
Goldman et al., "Algorithms for autonomous exploration and estimation in compliant environments," Robotica, 2012; 1-17.
Goldman et al., "Analysis, Algorithms, and Control for Intelligent Surgical Exploration and Intervention," Ph.D. Dissertation, (Advisor: N. Simaan), Mechanical Engineering, Columbia University, 2011; 1-148.
Goldman et al., "Compliant Motion Control for Continuum Robots with Intrinsic Actuation Sensing," in IEEE International Conference on Robotics and Automation, 2011, pp. 1126-1132.
Goldman et al., "Design and Performance Evaluation of a Minimally Invasive Telerobotic Platform for Transurethral Exploration and Intervention," ASME Journal on Medical Devices, vol. submitted, pp. 1-27, 2011.
Gossum et al., Capsule endoscopy versus colonoscopy for the detection of polyps and cancer. N Engl J Med, 361 (3):264-270, Jul. 2009.
Gwilliam et al., "Human vs. robotic tactile sensing: Detecting lumps in soft tissue," in IEEE Haptics Symposium, 2010, pp. 21-28.
Hall, Guyton and Hall Textbook of Medical Physiology, 2010.
Howe et al., "Remote palpation technology," IEEE Eng. Med. Biol. Mag., vol. 14, No. 3, pp. 318-323, 1995.
Inadomi et al., Adherence to colorectal cancer screening: A randomized clinical trial of competing strategies. Archives of Internal Medicine, 172(7):575-582, 2012.
Intuitive Surgical website: www.intuitivesurgical.com.
Kapoor et al., "Suturing in Confined Spaces: Constrained Motion Control of a Hybrid 8-DoF Robot", in IEEE International Conference on Advanced Robotics, 2005.
Kapoor et al., "Telemanipulation of Snake-Like Robots for Minimally Invasive Surgery of the Upper Airway," in MICCAI 2006 workshop on medical robotics, 2006.

\* cited by examiner

REAL-TIME POSE AND MAGNETIC FORCE DETECTION FOR WIRELESS MAGNETIC CAPSULE

RELATED APPLICATIONS

This patent application is a national stage filing under 35 U.S.C. § 371 of International Application No. PCT/US2014/012086, filed on Jul. 17, 2014, which application claims the benefit of U.S. Provisional Patent Application No. 61/753,755, filed Jan. 17, 2013, entitled "REAL-TIME POSE AND MAGNETIC FORCE DETECTION FOR WIRELESS MAGNETIC CAPSULE," the entire contents of which are incorporated herein by reference.

BACKGROUND

Magnetic coupling is one of the few physical phenomena capable of transmitting actuation forces across a physical barrier. In medicine, remote magnetic manipulation has the potential to make surgery less invasive by allowing untethered miniature devices to enter the body through natural orifices or tiny incisions and then maneuver with minimum disruption to healthy tissue. Magnetic coupling between a permanent magnet embed onboard the medical device and an external magnetic field source allows the medical device to be moved within the body of a patient.

One type of insertable medical device that utilizes magnetic coupling for locomotion is a magnetic capsule used for controlled endoscopy or for site-specific drug delivery. These capsules are inserted into the body of a patient and an external magnetic field is applied to move the magnetic capsule through the body.

SUMMARY

Knowing the pose (i.e., the position and orientation) of the insertable medical device helps the external magnetic field source control the position and movement of the medical device in the body of a patient. However, due to the strong magnetic link required for effective device manipulation, localization techniques based on electromagnetic fields are not adequate. The magnetic field that is applied to cause locomotion of the magnetic capsule prevents external systems from accurately determining in real-time the location and pose of the magnetic capsule inside the body of a patient.

The system described herein determines the position, the orientation, and the pressure exerted on surrounding tissues by a magnetic capsule inside the body. A set of sensors (e.g., a magnetometer, inertial sensors, etc.) are placed inside the magnetic capsule. Information detected by these sensors is wirelessly transmitted to an external system in real-time. The external system then determines the location and pose of the magnetic capsule based on the received information from the capsule sensors.

In one embodiment, the invention provides a method for determining an orientation and position of a capsule inserted into the body of a patient. A magnetic field is applied to an area of the patient where the capsule is located. Sensor data, including inertial data from an inertial sensor and magnetic field data indicative of the applied magnetic field as detected by at least one magnetic field sensor, is wirelessly received from the capsule. An orientation angle of the capsule is determined based at least in part on the inertial data. The magnetic field data is compared to known characteristics of the applied magnetic field and a location of the capsule is determined based on the comparison.

In another embodiment, the invention provides a capsule position-determining system for determining an orientation and position of a capsule inserted into the body of a patient. The capsule position-determining system includes an inertial sensor mounted on the capsule, at least one magnetic field sensor mounted on the capsule, a wireless transmitter mounted inside the capsule, and a controller. The controller is configured to receive sensor data from the inertial sensor and the at least one magnetic field sensor and to transmit the sensor data to an external system through the wireless transmitter.

Other aspects of the invention will become apparent by consideration of the detailed description and accompanying drawings and appendices.

BRIEF DESCRIPTION OF THE DRAWINGS AND APPENDICES

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
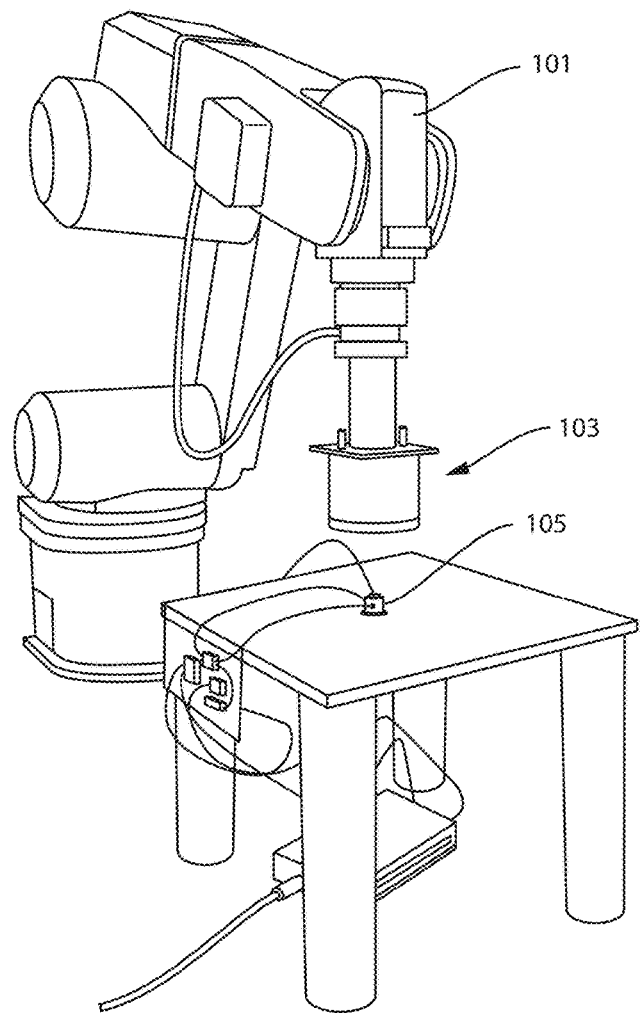
FIG. 1A is a perspective view of a robot arm for controlling the movement of the magnetic capsule externally.

FIG. 1A shows an industrial robotic arm 101. A cylindrical driving magnet 103 (e.g., an external permanent magnet (EPM)) is coupled to the distal end of the robotic arm 101. A magnetic capsule 105 is shown proximate to the cylindrical driving magnet 103. As described in further detail below, the magnetic capsule 105 can be inserted into the body of a patient—either surgically or through a natural orifice such as the mouth. In some constructions, the magnetic capsule naturally moves through the body of the patient until it reaches a target location (e.g., through the digestive tract) where, for example, an operation is performed or a medication is dispensed. In other constructions, the robotic arm 101 manipulates the cylindrical driving magnet 103. By magnetic attraction, the cylindrical driving magnet 103 controllably causes the magnetic capsule to move within the body of the patient to the target location.

Figure 1B:
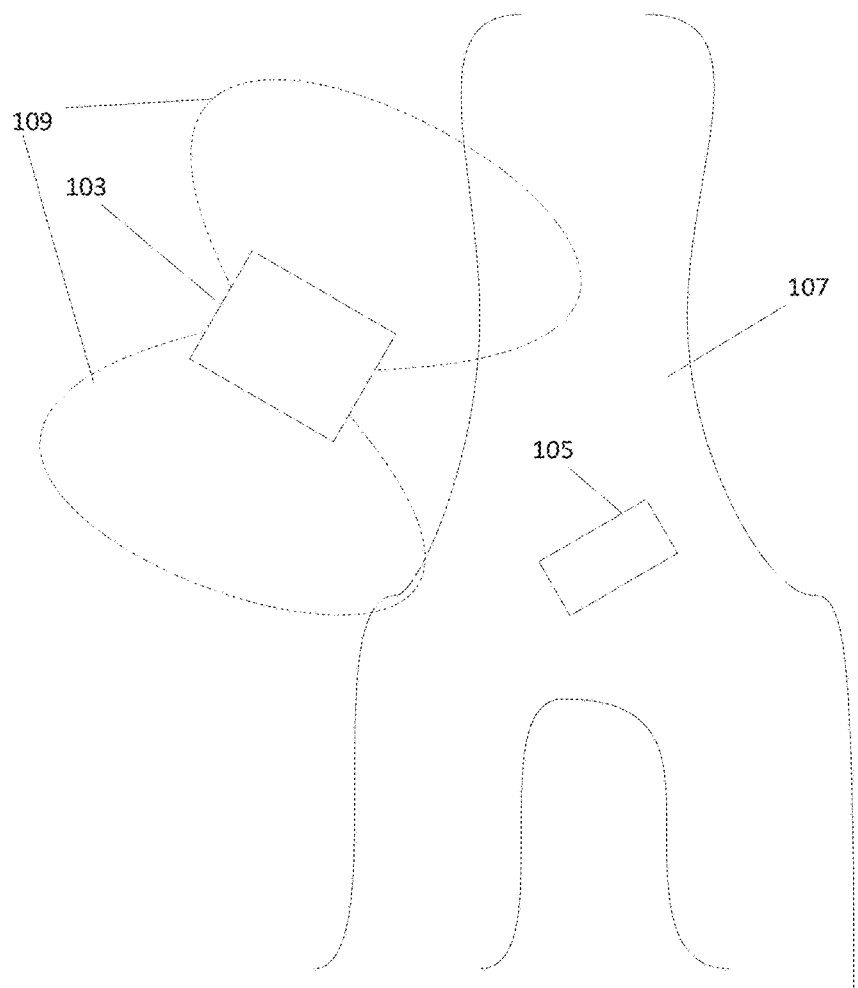
FIG. 1B is a schematic diagram of an external magnet of FIG. 1A controlling the movement of the magnetic capsule through a body cavity.
Figure 1C:
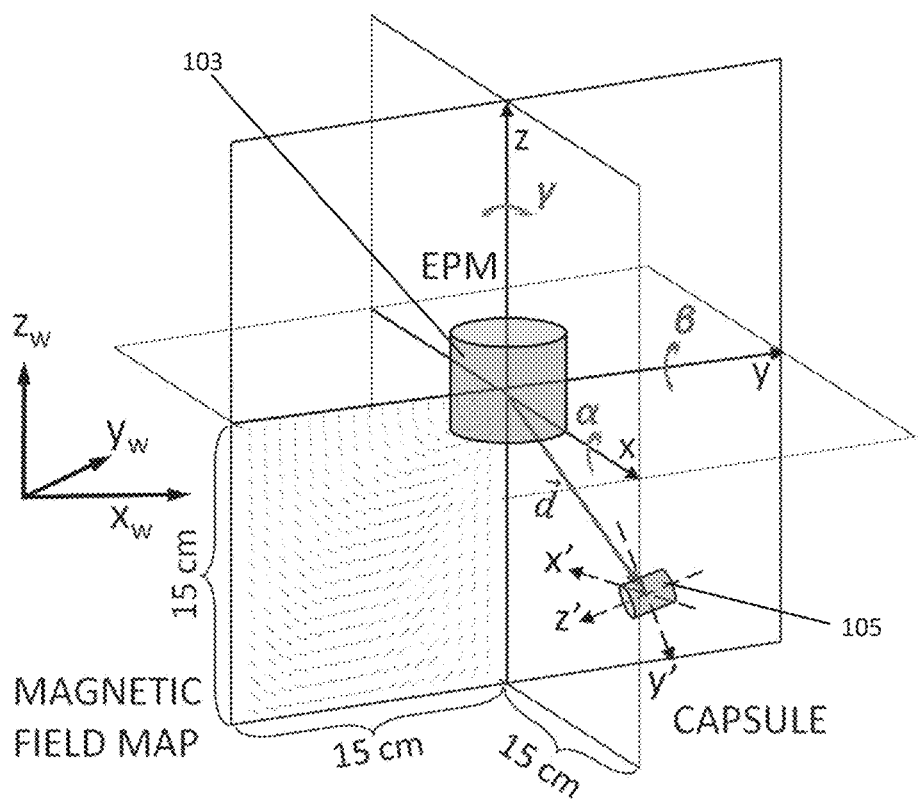
FIG. 1C is a graph of a magnetic field generated by the external magnet of FIG. 1A.

FIG. 1B shows the capsule 105 positioned within a body cavity 107 of a patient. The external cylindrical driving magnet 103 generates a magnetic field 109 that acts upon the capsule 105. FIG. 1C shows a more detailed graph of the magnetic field created by the driving magnet 103 and how the capsule 105 sits within the magnetic field.

As noted above, this magnetic field can be manipulated to cause a magnetic capsule 105 to move within the body cavity 107. However, because the magnetic field created by the driving magnet 103 is predictable and controllable, magnetic field sensors integrated into the capsule 105 can be used to identify the orientation of the capsule 105 within the magnetic field. As such, the orientation, position, and location of the capsule 105 within the body cavity can be accurately determined. This information can then be used to safely control the movement and operation of the capsule 105 within the body.

Figure 2A:
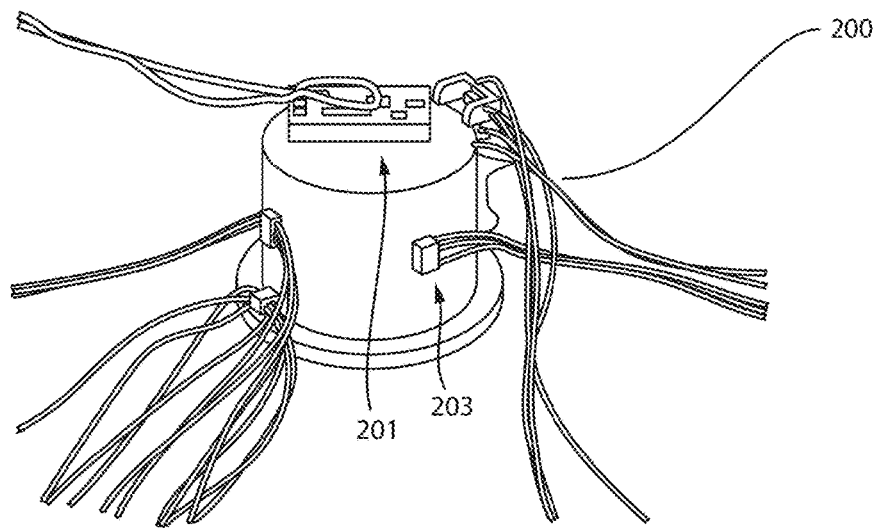
FIG. 2A is a perspective view of a magnetic capsule that can be moved by the robotic arm of FIG. 1.

FIG. 2A shows a perspective view of one example of a magnetic capsule 200. The capsule 200 includes a triaxial accelerometer 201 positioned on one end of the capsule 200 and a number of magnetic field sensors 203 positioned around the capsule 200. However, other constructions of the capsule 200 may use other types of inertial sensors such as, for example, a gyroscopic sensor or a combination IMU (inertial measurement unit) that includes both acceleration sensors and gyroscopic components. Although the sensors are shown at the surface of the capsule in the example of FIG. 2A, the arrangement and position of the sensors can be changed in other constructions of the magnetic capsule 200. Furthermore, in some constructions, a protective casing is formed around the exterior of the capsule and the sensors are positioned below the protective casing.

Figure 2B:
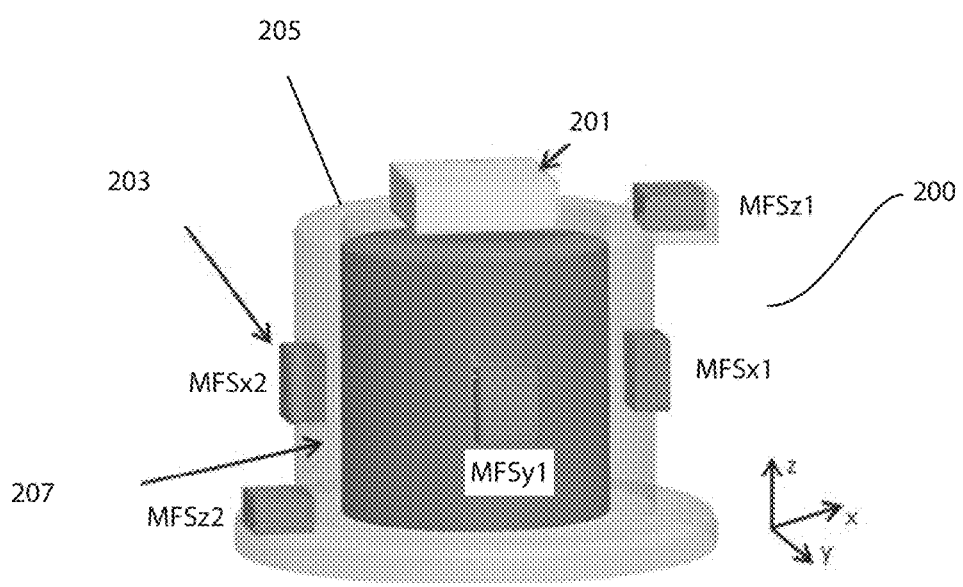
FIG. 2B is a partial cutaway view of the magnetic capsule of FIG. 2.

FIG. 2B provides a partial cutaway view of the capsule 200 to better illustrate the different sensors and their locations. Again, the triaxial accelerometer 201 is positioned at the top of the magnetic capsule 200. A series of uniaxial magnetic field sensors 203 are arranged in pairs around the magnetic capsule 200. Each pair of magnetic field sensors 203 corresponding to one Cartesian of the directions—MFSx1 and MFSx2 for the x-axis, MFSy1 and MFSy2 for the y-axis, and MFSz1 and MFSz2 for the z-axis. Sensor MFSx1 is positioned on one side of the magnetic capsule while sensor MFSx2 is positioned on the opposite side of the capsule. Sensors MFSy1 and MFSy2 (not shown) are also positioned at opposite sides of the magnetic capsule and arranged perpendicular to the MFSx1 and MFSx2 sensor pair. Sensors MFSz1 is positioned at the top of the capsule while corresponding sensor MFSz2 is positioned at the bottom of the capsule. The various sensors are attached to or set within a housing 205. As described in further detail below, a controller is positioned within the housing 205 that receives data from the various sensors and transmits that data to a processing or control system outside of the patient's body.

Figure 3:
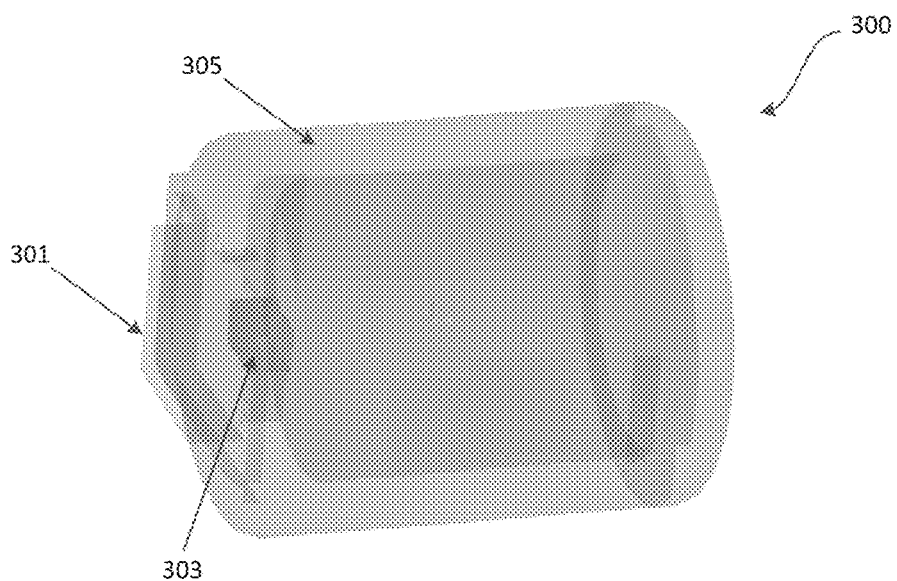
FIG. 3 is a partially transparent view of a capsule capable of detecting position with five degrees-of-freedom.

Instead of utilizing multiple single-axis magnetic field sensors, the capsule can include one or more tri-axial magnetic field sensors. For example, FIG. 3 illustrates a capsule 300 that includes a tri-axial accelerometer 301 and a tri-axial magnetic field sensor 303 both mounted on the same end of the capsule housing 305. The magnetic field sensor 303 provides three orthogonal measurements of the magnetic field. The data provided by the accelerometer 301 and the magnetic field sensor 303 allow the system to determine the pose and orientation of the capsule with five degrees-of-freedom.

Figure 4:
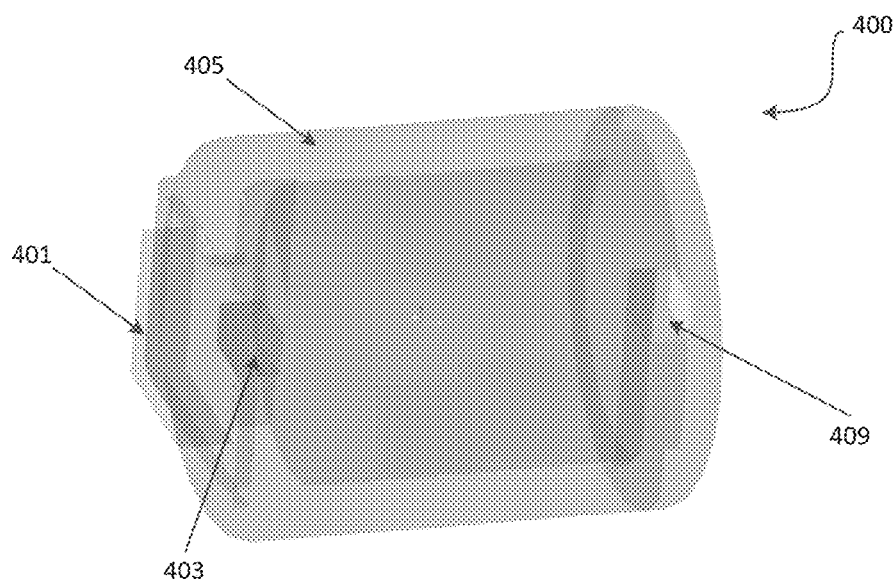
FIG. 4 is a partially transparent view of a capsule capable of detecting position with six degrees-of-freedom.

FIG. 4 illustrates an example of a capsule 400 that again includes a tri-axial accelerometer 401 and a tri-axial magnetic field sensor 403 both positioned at the same end of a capsule housing 405. However, the capsule 400 is equipped with a second tri-axial magnetic field sensor 409 positioned at the opposite end of the capsule housing 405. The inclusion of a second tri-axial magnetic field sensor allows the data to better determine all three tilt angles (i.e., yaw, pitch, and roll) of the magnetic capsule based on the difference between the magnetic fields detected by the two sensor (e.g., the x-axis field detected by sensor 403 compared to the x-axis field detected by sensor 409). Without the benefit of the second tri-axial magnetic field sensor, the device is only capable of determining two of the tilt angles.

Figure 5:
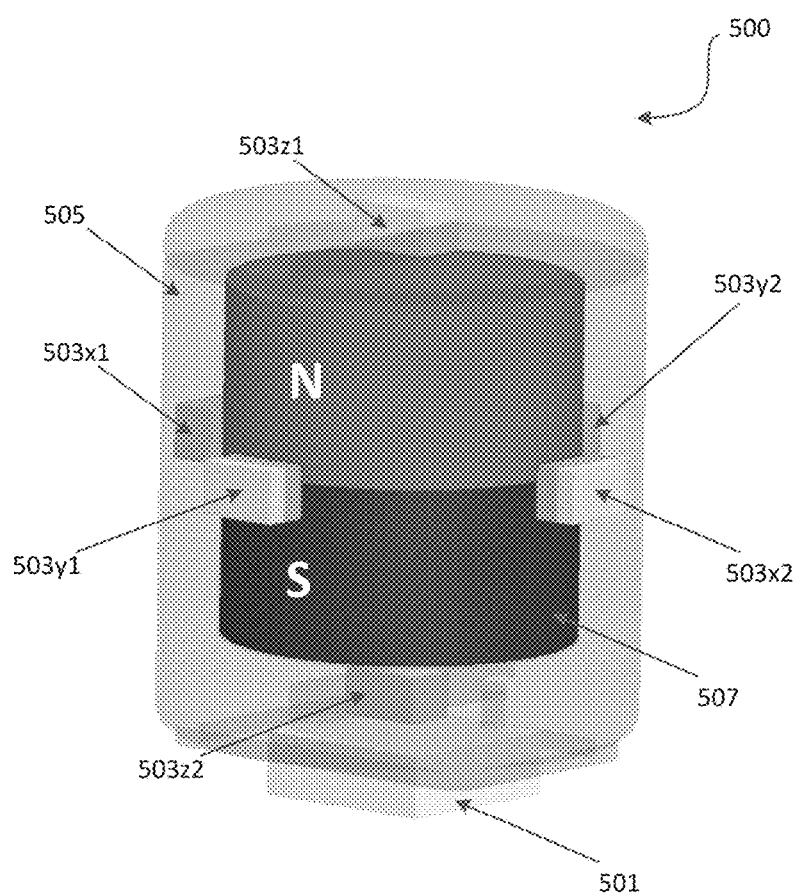
FIG. 5 is a partially transparent view of a capsule capable of detecting position with six degrees-of-freedom and of being moved by the robotic arm of FIG. 1.

FIG. 5 illustrates another example of a capsule 500. This capsule 500 includes a tri-axial accelerometer 501 and a series of six single-axis magnetic field sensors 503 positioned around the capsule housing 505. Like the example of FIG. 2B, the single-axis magnetic field sensors are arranged in axis pairs around the capsule housing 505. Sensors 503$x$1 and 503$x$2 are positioned on opposite sides of the housing 505 and monitor the x-axis magnetic field. Sensors 503$y$1 and 503$y$2 are positioned on opposite sides of the housing 505—perpendicular to sensors 503$x$1 and 503$x$2—and monitor the y-axis magnetic field. Sensors 503$z$1 and 503$z$2 are positioned on the top and bottom of the capsule housing 505, respectively, and monitor the z-axis magnetic field.

The capsule 500 of FIG. 5 also includes a permanent magnet 507 positioned within the capsule housing 505. The permanent magnet 507 allows the capsule to be controlled and moved by the external magnet on the robotic arm. In contrast, the capsules illustrated in FIGS. 3 and 4 do not include internal permanent magnets. As such, an external driving magnet cannot be used to control the position of the capsules 300 and 400. Instead, the magnetic field generated by the external magnetic can only be used to determine the location, position, and orientation of the capsule 300 and 400.

Because the internal permanent magnet 507 of capsule 500 is attracted to the external magnet, magnetic forces generated by the external magnet will act upon the capsule 500 and cause it to move within the body of the patient. In addition to detecting the position and orientation of the capsule, the sensor arrangement of capsule 500 allows the system to monitor the magnetic force.

Figure 6:
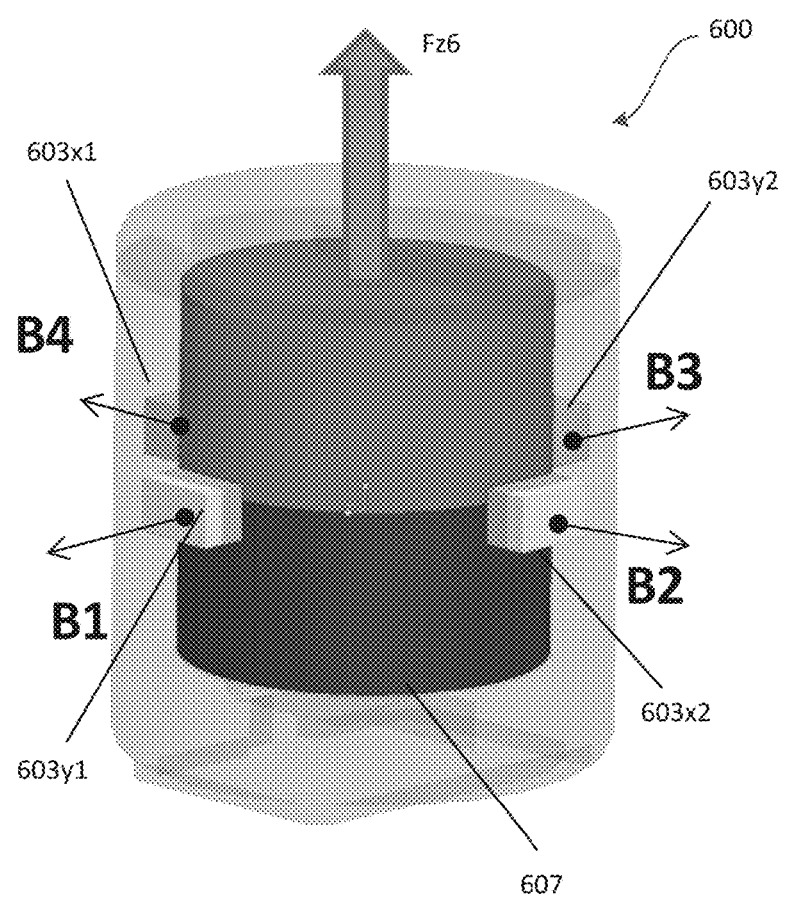
FIG. 6 is a partially transparent view of a capsule capable of being moved by the robotic arm of FIG. 1 and detecting axial force acting on the capsule with one degree-of-freedom.
Figure 7:
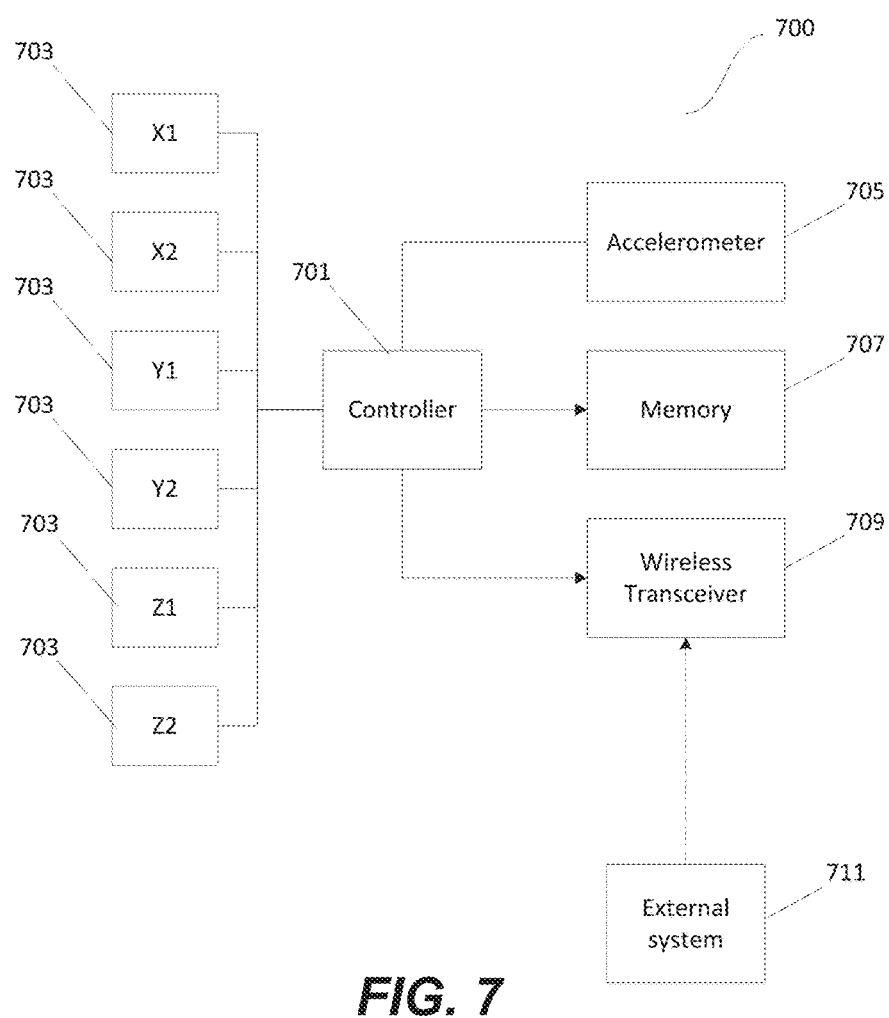
FIG. 7 is a block diagram of a control system for a magnetic capsule with position detection functionality.

FIG. 6 shows an example of the capsule 600 with only four single-axis magnetic field sensors—603$x$1, 603$x$2, 603$y$1, and 603$y$2—and an internal permanent magnet 607. Each magnetic field sensor measures a single-axis magnetic field—B1, B2, B3, and B4—in real-time. These sensor measurements are used to calculate the magnetic force acting on the capsule in the z-axis (Fz6) using the following equation:

$$Fz6 = B1*Gk + B2*Gk - B3*Gk - B4*Gk \tag{1}$$

where Gk is a calibration constant that is determined experimentally to account for the volume of the magnet 607

(pi/2*radius*height) and its magnetic properties such as Br0, vacuum magnetic constant, and calibration model coefficients.

The capsule 600 can be implemented as a simplified magnetic force detection system and includes only the four magnetic field sensors as illustrated in FIG. 6. Alternatively, more advanced and complex capsule systems, such as the capsule 500 illustrated in FIG. 5 can utilize the x-axis and y-axis magnetic field sensors to calculate magnetic force in the z-axis. Furthermore, systems such as capsule 500 can monitor the other components (x and y) of the magnetic force acting on the capsule 500.

In order to communicate the sensor readings to an external system where they can be processed, each capsule is equipped with an electronic control system 700. The control system includes a controller 701 that receives magnetic field information from each of the magnetic field sensors 703 and the tri-axial accelerometer 705.

The controller 701 may include an internal memory for storing sensor data and program instructions. Alternatively, the controller 701 may include a processor that communicates with a non-transient memory module 707. The memory module 707 stores computer-executable instructions that are executed by the control 701 to perform the various operations such as described herein.

The controller 701 transmits the sensor data through a wireless transceiver 709 to an external system 711 where it is processed and analyzed. The memory 707 can be used to store the sensor data at least until a wireless communication link is established with the external system 711. In some other constructions, the sensor data can be communicated to an external system 711 through a wired communication interface such as a "soft tether" with an electrical cable housed inside. Furthermore, in some embodiments, the controller 701 may also be configured to receive data from the external system 711 through the wireless transceiver 709. Such received data can include, for example, instructions for controlling an operation of the capsule such as dispensing medication.

Figure 8:
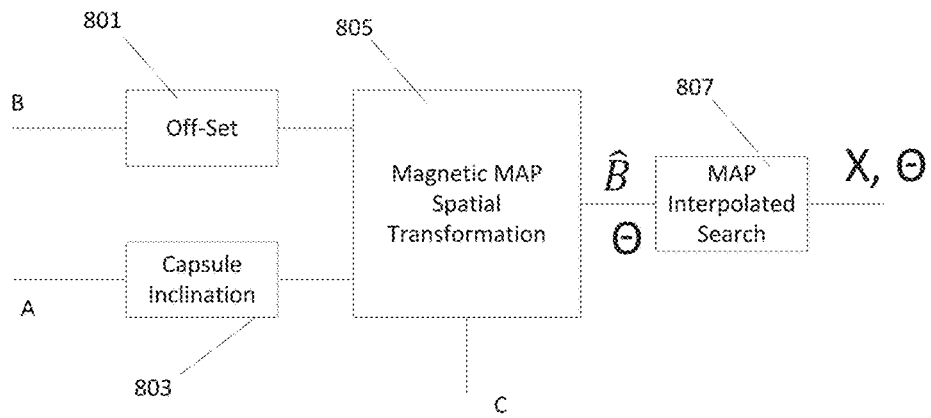
FIG. 8 is a flow chart of a method of determining absolute position of a magnetic capsule.
Figure 9:
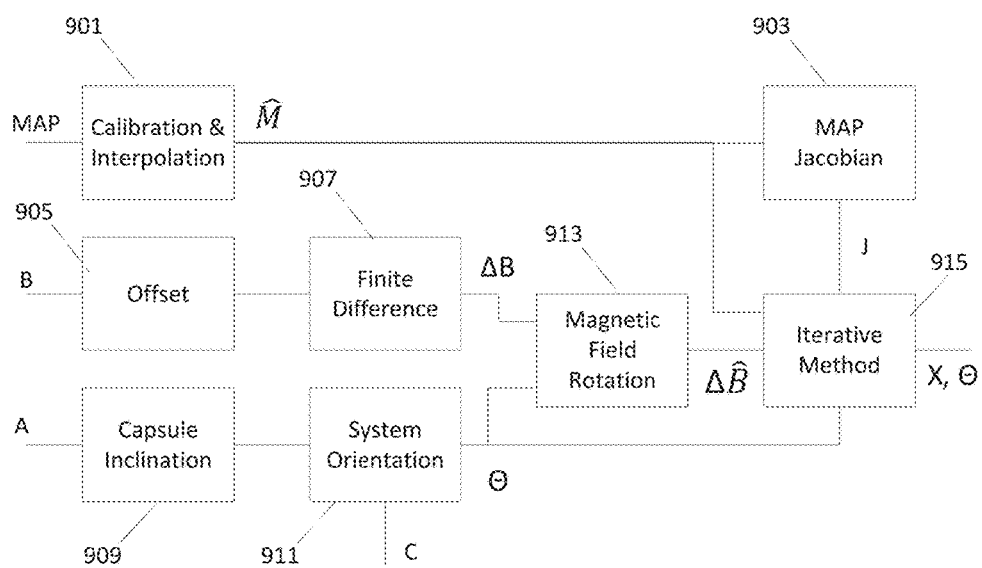
FIG. 9 is a flow chart of a method of determining the position of a magnetic capsule based on iterative changes in position and orientation.

Once the external system 711 receives the sensor data, the data is processed to determine the location, position, and orientation of the capsule within the body cavity. FIGS. 8 and 9 illustrate two examples of method that use the magnetic field and accelerometer data gathered by the capsule sensors to determine localization of the capsule.

FIG. 8 uses the data to determine an absolute position of the capsule with respect to an external fixed reference frame. The magnetic field data measurements B are received from the magnetic field sensors. If the capsule includes an internal permanent magnet, the magnetic field data measurements are offset (step 801) such that they represent only the magnetic field applied by the external driving magnet. The inertial measurements A from the tri-axial accelerometer are analyzed to determine the inclination/orientation of the capsule (step 803). A rigid transformation (i.e., rotations) of a pre-compiled magnetic field matrix is performed (step 805) to align a precompiled magnetic field matrix with the external magnet field source orientation and the measured capsule orientation. The external magnet field source orientation is determined based on a position of the external magnet as determined by the pose of the robotic arm and the orientation of the external magnet as determined by an inertial sensor coupled to the end effector of the robotic arm. The elaborated magnetic field (B^) and the known capsule orientation are then used to compute an appropriate interpolation of the magnetic field MAP with the elaborated magnetic field (B^) (step 807). The output of this interpolation is a capsule position X (including x, y, and z Cartesian coordinates) and the capsule orientation θ (including rotations around the three Cartesian axes).

FIG. 9 illustrates an alternative method for determining the position and orientation of the capsule using an iterative approach. The magnetic field model MAP of the external driving magnet is calibrated and interpolated to reduce the matrix dimensions (step 901). The Jacobian of the magnetic MAP is also derived (step 903). The magnetic field sensor measurements B are offset to account for changes in the magnetic field caused by the permanent magnet installed within the capsule (step 905). The offset magnetic field sensor measurements are then compared to a previous set of magnetic field measurements to determine a change in the magnetic field (ΔB) (step 907). The inertial data from the tri-axial accelerometer A is again used to determine the capsule inclination θ (step 909). The relationship between the capsule orientation and the orientation of the applied magnetic field C is characterized based on the pose of the external magnet (as determined by the pose of the robotic arm and the orientation of the external magnetic as indicated by an inertial sensor coupled to the end effector of the robotic arm (step 911). The change in magnetic field (ΔB) and the capsule orientation θ are then used to generate a spatial transformation allying the capsule orientation with the magnetic field measured by the capsule itself (step 913).

An iterative method is used to determine the capsule change in pose ΔX (tri-dimensional displacement) and Δθ(tri-dimensional rotation). This can be used to derive the absolute pose X (including Cartesian coordinates x, y, and z) and θ (including rotations around the three Cartesian axes) through iterative integration and inversion of the MAP image (which is given by the Jacobian J) (step 915). As a result, the capsule change in pose is determined based on changes in the measured magnetic field instead of an absolute analysis of the magnetic field thus reducing computational load.

Localization algorithms utilizing this system have experimentally been able to provide an accuracy of 8 mm in position detection, one degree for roll and pitch detection, and 2.5 degrees for yaw detection within a spherical workspace of 15 cm in radius centered on the driving magnet. Computational time is 2 ms.

Figure 10:
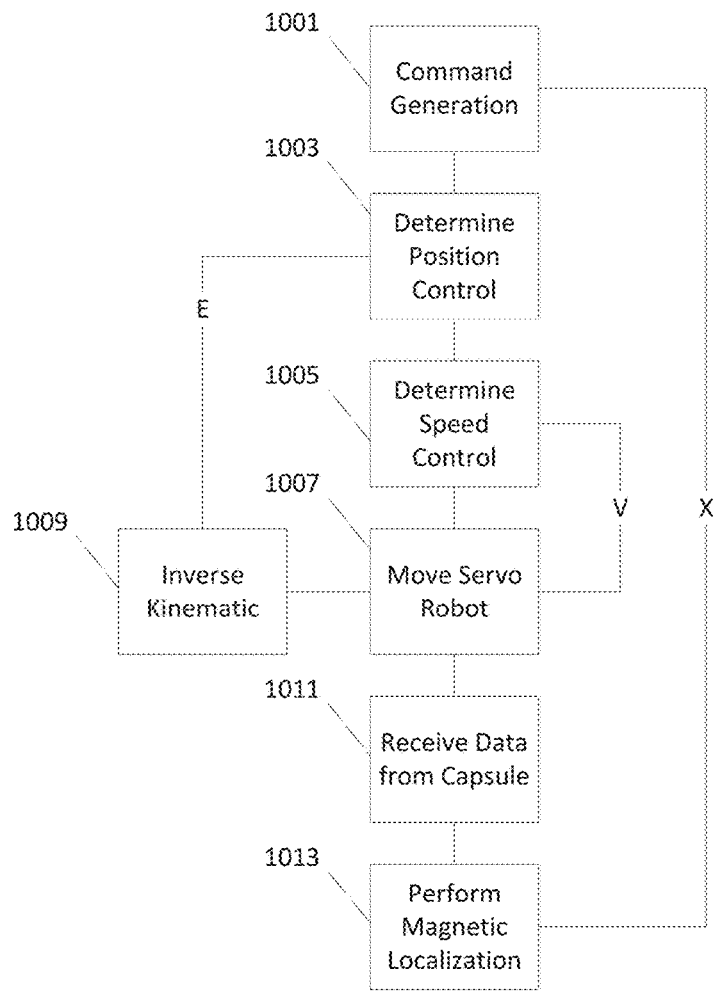
FIG. 10 is a flow chart of a method of operating the robotic arm of FIG. 1 to control the movement of a magnetic capsule.

Although, in the examples of FIGS. 8-10, the controller in the magnetic capsule only sends sensor readings to the external controller, in other constructions the controller in the magnetic capsule may be configured to analyze the sensor readings to determine the location and orientation of the capsule. The location and orientation information is then wireless transmitted from the capsule controller to an external controller.

The determined orientation, position, and speed of the magnetic capsule through the body cavity can provide feedback to the control system (i.e., the robotic arm with the driving magnet) to safely maneuver the capsule through the body of the patient. FIG. 10 provides an example of one such closed-loop robotic control mechanism. A movement command is generated (step 1001) either through user input or by an automated movement protocol. The system determines a robotic control maneuver necessary to achieve a desired position change (step 1003) and determines an appropriate speed control (step 1005). The robotic control system then activates the servo motor to move the robotic arm according to the position and speed controls (step 1007). The velocity V of the robotic arm end effector fed back to adjust the speed control (step 1005) and an inverse kinematic analysis (step 1009) of the position of the robotic arm is used to adjust the position control (step 1003).

As magnetic field and inertial data are received from the capsule (step 1011), the control system analyzes the data to determine the position and orientation of the capsule (step 1013)—for example, according to the absolute localization method of FIG. 8 or the iterative localization method of FIG. 9. The location X of the capsule is used by the next iteration of the command generation to determine the next appropriate step to safely move the capsule to a target location.

Thus, the invention provides, among other things, a systems and methods for determining the location and position of a capsule in the body of a patient based on information detected from a series of sensors coupled to the capsule and wireless communicated to an external controller. Various features and advantages of the invention are set forth in the following claims and the attached appendices.

What is claimed is:

1. A method of determining an orientation and position of a capsule inserted into a body of a patient, the method including:
    applying a magnetic field to an area of the patient where the capsule is located, wherein the magnetic field is applied by an external permanent magnet coupled to a distal end of a robotic arm;
    causing movement of the capsule by manipulating the robotic arm to change a pose of the external permanent magnet, wherein the capsule includes an internal permanent magnet that is attracted to the external permanent magnet of the robotic arm and moves in response to an applied magnetic force and/or torque from the external permanent magnet;
    receiving sensor data from the capsule, the sensor data including inertial data from an inertial sensor mounted on the capsule and magnetic field data indicative of the applied magnetic field as detected by at least one magnetic field sensor mounted on the capsule;
    determining an orientation angle of the capsule based at least in part on the inertial data;
    determining an orientation angle of the external permanent magnet based on a controlled pose of the robotic arm;
    generating an interpolated magnetic field map by performing a rigid transformation of a precompiled magnetic field matrix to align the precompiled magnetic field matrix with the capsule based on the determined orientation angle of the capsule and the determined orientation angle of the external permanent magnet, wherein the precompiled magnetic field matrix indicates a magnetic field applied by the external permanent magnet at each of a plurality of locations relative to the external permanent magnet;
    comparing the magnetic field data to the interpolated magnetic field map; and
    determining a location of the capsule based on the comparison of the magnetic field data and the interpolated magnetic field map.

2. The method of claim 1, wherein the at least one magnetic field sensor includes a tri-axial magnetic field sensor.

3. The method of claim 1, wherein the at least one magnetic field sensor includes two tri-axial magnet field sensors mounted on opposite ends of the capsule.

4. The method of claim 1, wherein the act of receiving sensor data from the capsule includes receiving magnetic field data from each of six single-axial magnetic field sensors, wherein a first pair of the single-axial magnetic field sensors are mounted on opposite ends of the capsule along an x-axis of the capsule, wherein a second pair of the single-axial magnetic field sensors are mounted on opposite ends of the capsule along a y-axis of the capsule, and wherein a third pair of the single-axial magnetic field sensors are mounted on opposite ends of the capsule along a z-axis of the capsule.

5. The method of claim 1, wherein the act of receiving sensor data from the capsule includes receiving inertial data from a tri-axial accelerometer mounted at one end of the capsule.

6. The method of claim 1, wherein the act of receiving sensor data from the capsule includes receiving magnetic field data from four single-axis magnetic field sensors positioned at equal intervals around the capsule.

7. The method of claim 6, wherein the four single-axis magnetic field sensors includes
    a first magnetic field sensor and a second magnetic field sensor positioned on opposite sides of the capsule along an x-axis of the capsule and configured to detect a magnetic field in a direction of the x-axis, and
    a third magnetic field sensor and a fourth magnetic field sensor positioned on opposite sides of the capsule along a y-axis of the capsule and configured to detect a magnetic field in a direction of the y-axis,
the method further comprising determining a magnetic force applied to the capsule in a direction of a z-axis of the capsule due to the magnetic attraction between the internal permanent magnet of the capsule and the external permanent magnet of the robotic arm based on a single-axis magnetic field detected by each of the four single-axis magnetic field sensors.

8. The method of claim 7, wherein determining the magnetic force includes calculating a magnetic force according to the equation:

$$Fz = B1*Gk + B2*Gk - B3*Gk - B4*Gk$$

wherein Fz is the magnetic force in the direction of the z-axis of the capsule, B1 is a magnetic field detected by the first magnetic field sensor mounted on the x-axis of the capsule, B2 is a magnetic field detected by the second magnetic field sensor mounted on the x-axis of the capsule opposite the first magnetic field sensor, B3 is a magnetic field detected by the third magnetic field sensor mounted on the y-axis of the capsule, B4 is a magnetic field detected by the fourth magnetic field sensor mounted on the y-axis of the capsule opposite the third magnetic field sensor, and Gk is a calibration constant tuned for the capsule.

9. The method of claim 1, further comprising:
    receiving internal magnetic field data based on a magnetic field applied to the at least one magnetic field sensor by the internal permanent magnet of the capsule;
    calculating offset magnetic field data indicative of only the magnetic field applied to the capsule by the external permanent magnet, wherein the offset magnetic field data is calculated based on the internal magnetic field data, and
    wherein comparing the magnetic field data to the interpolated magnetic field map includes comparing the offset magnetic field data to the interpolated magnetic field map.

10. A capsule position-determining system for determining an orientation and position of a capsule inserted into a body of a patient, the capsule position-determining system comprising:

an inertial sensor mounted on the capsule, the capsule being insertable into a body cavity of the patient;

an internal permanent magnet mounted to the capsule;

at least one magnetic field sensor mounted on the capsule, the at least one magnetic field sensor configured to detect a magnetic field applied to the body of the patient by an external permanent magnet;

a wireless transmitter mounted inside the capsule; and a controllable robotic arm, the external permanent magnet mounted on a distal end of the robotic arm; and a controller configured to cause movement of the capsule by manipulating the robotic arm to change a pose of the external permanent magnet, wherein the internal permanent magnet is attracted to the external permanent magnet and the capsule moves in response to an applied magnetic force and/or torque from the external permanent magnet, receive sensor data from the capsule, the sensor data including an output of the at least one magnetic field sensor and an output of the inertial sensor, determine an orientation angle of the capsule based at least in part on the output of the inertial sensor, determine an orientation angle of the external permanent magnet based on a controlled pose of the robotic arm, generate an interpolated magnetic field map by performing a rigid transformation of a precompiled magnetic field matrix to align the precompiled magnetic field matrix with the capsule based on the determined orientation angle of the capsule and the determined orientation angle of the external permanent magnet, wherein the precompiled magnetic field matrix indicates a magnetic field applied by the external permanent magnet at each of a plurality of locations relative to the external permanent magnet, compare sensed magnetic field data based on the output of the at least one magnetic field sensor to the interpolated magnetic field map, and determine a location of the capsule based on the comparison of the sensed magnetic field data and the interpolated magnetic field map.

11. The capsule position-determining system of claim 10, wherein the at least one magnetic field sensor includes a tri-axial magnetic field sensor mounted on a first end of the capsule.

12. The capsule position-determining system of claim 11, wherein the at least one magnetic field sensor further includes a second tri-axial magnetic field sensor mounted on a second end of the capsule opposite the first end of the capsule.

13. The capsule position-determining system of claim 10, wherein the at least one magnetic field sensor includes a first pair of single-axial magnetic field sensors mounted on opposite ends of the capsule along an x-axis of the capsule, a second pair of single-axial magnetic field sensors mounted on opposite ends of the capsule along a y-axis of the capsule, and a third pair of single-axial magnetic field sensors mounted on opposite ends of the capsule along a z-axis of the capsule.

14. The capsule position-determining system of claim 10, wherein the at least one magnetic field sensor includes a first pair of single-axial magnetic field sensors mounted on opposite ends of the capsule along an x-axis of the capsule, a second pair of single-axial magnetic field sensors mounted on opposite ends of the capsule along a y-axis of the capsule, and wherein the controller is further configured to determine a magnetic force applied to the capsule in a direction of a z-axis of the capsule due to magnetic attraction between the internal permanent magnet of the capsule and the external permanent magnetic based on a single-axis magnetic field detected in a direction of the x-axis by the first pair of single-axial magnetic field sensors and a single-axis magnetic field detected in a direction of the y-axis by the second pair of single-axial magnetic field sensors.

\* \* \* \* \*